US006794490B2

(12) United States Patent
Hill et al.

(10) Patent No.: US 6,794,490 B2
(45) Date of Patent: Sep. 21, 2004

(54) LIPOPEPTIDES AS ANTIBACTERIAL AGENTS

(75) Inventors: Jason Hill, Auburndale, MA (US); Ian Parr, Medford, MA (US); Michael Morytko, Framingham, MA (US); Jim Siedlecki, Burlington, MA (US); Xian Yang Yu, Billerica, MA (US); Jared Silverman, Brookline, MA (US); Dennis Keith, Arlington, MA (US); John Finn, Stow, MA (US); Dale Christensen, Apex, NC (US); Tsvetelina Lazarova, Brookline, MA (US); Alan D. Watson, Lexington, MA (US); Yan Zhang, Sharon, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 120 days.

(21) Appl. No.: 09/739,535

(22) Filed: Dec. 15, 2000

(65) Prior Publication Data

US 2002/0058785 A1 May 16, 2002

Related U.S. Application Data

(60) Provisional application No. 60/170,945, filed on Dec. 15, 1999.

(51) Int. Cl.[7] .............................................. A61K 38/12

(52) U.S. Cl. ......................... 530/317; 514/11; 514/14; 530/327; 530/332

(58) Field of Search .................................. 530/317, 327, 530/332; 514/11, 14

(56) References Cited

U.S. PATENT DOCUMENTS

| 4,396,543 A | 8/1983 | Debono ............... 260/112.5 R |
| 4,399,067 A | 8/1983 | Debono ............... 260/112.5 R |
| 4,482,487 A | 11/1984 | Abbott et al. ......... 260/112.5 R |
| 4,524,135 A | 6/1985 | Abbott et al. ................. 435/69 |
| 4,537,717 A | 8/1985 | Abbott et al. ......... 260/112.5 R |
| RE32,310 E | 12/1986 | Debono ...................... 530/317 |
| RE32,311 E | 12/1986 | Debono ...................... 530/317 |
| 5,573,936 A | 11/1996 | Kreuzman et al. .......... 435/196 |
| 5,629,288 A | 5/1997 | Lattrell et al. ................. 514/9 |
| 5,912,226 A | 6/1999 | Baker et al. ................... 514/9 |

FOREIGN PATENT DOCUMENTS

| EP | 095 295 A1 | 11/1983 |
| EP | 0 885 957 A1 | 12/1998 |
| WO | WO 99/43700 | 9/1999 |

OTHER PUBLICATIONS

Alborn, W E Jr et al . "Daptomycin Disrupts Membrane Potential in Growing *Staphylococcus aureus,*" *Antimicrobial Agents and Chemotherapy* 35 2282–2287 (1991).

Allen, N E et al "Inhibition of Peptidoglycan Biosynthesis in Gram–Positive Bacteria by LY146032." *Antimicrobial Agents and Chemotherapy* 31 1093–1099 (1987).
Allen, N E et al "Inhibition of Membrane Potential–Dependent Amino Acid Transport by Daptomycin," *Antimicrobial Agents and Chemotherapy* 35 2639–2642 (1991).
Baltz, R H , "Lipopeptide Antibiotics Produced by *Streptomyces roseosporus* and *Streptomyces fradite,*" in *Biotechnology of Antibiotics,* 2d Ed . 415–435 (1997).
Bingen, E et al "Bactericidal Activity of Daptomycin Against Vancomycin–Resistant *Enterococcus faecium* in an in Vitro Pharmacokinetic Model," *Eur. J. Clin. Microbiol. Infect. Dis.* 10 1062–1065 (1991).
Boeck, LaVerne D et al "Deacylation of A21978C, An Acidic Lipopeptide Antibiotic Complex, by *Actinoplanes utahensis,*" *Journal of Antibiotics* XLI 1085–1092 (1988).
Boeck, L D et al "A54145, A New Lipopeptide Antibiotic Complex Discovery, Taxonomy, Fermentation and HPLC," *Journal of Antibiotics* XLIII 587–593 (1990).
Champlin, Franklin R et al "Cell Envelope Impermeability to Daptomycin in *Pseudomonas aerugmosa* and *Pasteurella multocida,*" *Current Microbiology* 21 367–372 (1990).
Chong, Pei Pei et al "Physical Identification of a Chromosomal Locus Encoding Biosynthetic Genes for the Lipopeptide Calcium–Dependent Antibiotic (CDA) of *Streptomyces coelicolor* A3(2)," *Microbiology* 144 193–199 (1998).
Debono, M et al "A21978C, A Complex of New Acidic Peptide Antibiotics Isolation, Chemistry, and Mass Spectral Structure Elucidation." *Journal of Antibiotics* XL 761–777 (1987).
Debono, M et al. "Enzymatic and Chemical Modifications of Lipopeptide Antibioitic A21978C: The Synthesis and Evaluation of Daptomycin (LY146032)," *Journal of Antibiotics* XLI 1093–1105 (1988).
Debono, M et al "Synthesis of New Analogs of Echinocandin B by Enzymatic Deacylation and Chemical Reacylation of the Echinocandin B Peptide Synthesis of the Antifungal Agent Cilofungin (LY121019)." *Journal of Antibiotics* XLII 389–397 (1989).
Dong, Mei–Yan et al "Treatment of *Clostridnom difficile* Colitis in Hamsters with a Lipopeptide Antibiotic, LY146032," *Antimicrobial Agents and Chemotherapy* 31 1135–1136 (1987).
Eid, Pascale et al "Effect of Daptomycin on the Barotropic Behavior of Dioleoylphosphatidylglycerol An Infrared Spectroscopic Investigation," *Chemistry and Physics of Lipids* 83 131–140 (1996).

(List continued on next page.)

*Primary Examiner*—Christopher S. F. Low
*Assistant Examiner*—David Lukton
(74) *Attorney, Agent, or Firm*—Timothy J. Douros; Jill M.N. Mandelblatt

(57) ABSTRACT

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

26 Claims, No Drawings

OTHER PUBLICATIONS

Eliopoulos, George M et al "In Vitro Activity and Mechanism of Action of $A21978C_1$, a Novel Cyclic Lipopeptide Antibiotic," *Antimicrobial Agents and Chemotherapy* 27 357–362 (1985).

Huber, F M et al "The Formation of Daptomycin by Supplying Decanoic Acid to *Streptomyces roseosporus* Cultures Producing the Antibiotic Complex A21978C," *Journal of Biotechnology* 7 283–292 (1988).

Huber, F M et al "The Synthesis of A21978C Analogs by *Streptomyces roseosporus* Cultivated Under Carbon Limitation and Fed Fatty Acids," *Biotechnology Letters* 12 789–792 (1990).

Inokoshi, Junji et al "Cloning and Sequencing of the Aculeacin A Acylase–Encoding Gene From *Actmoplanes utahensis* and Expression in *Streptomyces lividans,*" *Gene* 119 29–35 (1992).

Inokoshi, Junji et al "Efficient Production of Aculeacin A Acylase in Recombinant *Streptomyces* strains," *Appl. Microbiol. Biotechnol* 39 532–536 (1993).

Kempter, Christoph et al "CDA Calcium–Dependent Peptide Antibiotics from *Streptomyees coelicolor* A3(2) Containing Unusual Residues," *Angew. Chem. Int. Ed. Engl* 36 498–501 (1997).

Kirsch, Lee E et al "Kinetics of the Aspartyl Transpeptidation of Daptomycin, A Novel Lipopeptide Antibiotic," *Pharmaceutical Research* 6 387–393 ( 1989).

Lakey, Jeremy H et al "The Role of Acyl Chain Character and Other Determinants on the Bilayer Activity of A21978C An Acidic Lipopeptide Antibiotic." *Biochimica et Biophysica Acta* 859 219–226 (1986).

Lakey, Jeremy H et al "Fluorescence Indicates a Calcium-Dependent Interaction Between the Lipopeptide antibiotic LY146032 and Phospholipid Membranes,"*Biochemistry* 27 4639–4645 (1988).

Lakey, Jeremy H et al "The Lipopeptide Antibiotic A21978C Has a Specific Interaction With DMPC Only in the Presence of Calcium Ions," *Biochimica et Biophysica Acta* 985 60–66 (1989).

Lee, Belle L. et al "Effect of Protein Binding of Daptomycin on MIC and Antibacterial Activity," *Antimicrobial Agents and Chemotherapy* 35 2505–2508 (1991).

Liebowitz, Lynne D et al. "In Vitro Selection of Bacteria Resistant to LY146032, a New Cyclic Lipopeptide," *Antimicrobial Agents and Chemotherapy* 32 24–26 (1988).

Maget–Dana, Regine et al. "A Comparative Monomolecular Film Study of Antibiotic A21978C Homologues of Various Lipid Chain Length," *Biochemica et Biophysica Acta* 962 201–207 (1988).

Zambias, Robert A et al "Preparation and Structure–Activity Relationships of Simplified Analogues of the Antifungal Agent Cilofungin A Total Synthesis Approach," *Journal of Medicinal Chemistry* 35: 2843–2855 (1992).

Zmijewski, M J et al "Role of Branched Chain Fatty Acid Precursors in Regulation Factor Profile in the Biosynthesis of A21978 C Complex," *Journal of Antibiotics* XXXIX 1483–1485 (1986).

Tally, T.P. et al., "Daptomycin: a Novel Agent for Gram-positive Infections," *Exp. Opin. Invest. Drugs* 8: 1223–1238 (1999).

LIPOPEPTIDES AS ANTIBACTERIAL AGENTS

FIELD OF THE INVENTION

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

BACKGROUND OF THE INVENTION

The rapid increase in the incidence of gram-positive infections—including those caused by resistant bacteria—has sparked renewed interest in the development of novel classes of antibiotics. A class of compounds which have shown potential as useful antibiotics includes the A-21978C lipopeptides described in, for example, U.S. Pat. Nos. RE 32,333; RE 32,455; RE 32,311; RE 32,310; U.S. Pat. Nos. 4,482,487; 4,537,717; and 5,912,226. Daptomycin, a member of this class, has potent bactericidal activity in vitro and in vivo against clinically relevant gram-positive bacteria that cause serious and life-threatening diseases. These bacteria include resistant pathogens, such as vancomycin-resistant enterococci (VRE), methicillin-resistant *Staphylococcus aureus* (NRSA), glycopeptide intermediate susceptible *Staphylococcus aureus* (GISA), coagulase-negative staphylococci (CNS), and penicillin-resistant *eptococcus pneumoniae* (PRSP), for which there are few therapeutic alternatives. See, e.g., Tally et al., 1999, *Exp. Opin. Invest. Drugs* 8:1223–1238.

Despite the promise that antibacterial agents such as daptomycin offer, the need for novel antibiotics continues. Many pathogens have been repeatedly exposed to commonly-used antibiotics This exposure has led to the selection of variant antibacterial strains resistant to a broad spectrum of antibiotics. The loss of potency and effectiveness of an antibiotic caused by resistant mechanisms renders the antibiotic ineffective and consequently can lead to life-threatening infections that are virtually untreatable. As new antibiotics come to market pathogens may develop resistance or intermediate resistance to these new drugs, effectively creating a need for a stream of new antibacterial agents to combat these emerging strains. In addition compounds that exhibit bacteriacidal activity would offer advantages over present bacteriastatic compounds. Thus, novel synthetic antibacterial agents would be expected to be useful to treat not only "natural" pathogens, but also intermediate drug resistant and drug resistant pathogens because the pathogen has never been exposed to the novel antibacterial agent. Additionally, new antibacterial agents may exhibit differential effectiveness against different types of pathogens.

SUMMARY OF THE INVENTION

The present invention addresses this problem by providing novel lipopeptide compounds which have antibacterial activity against a broad spectrum of bacteria, including drug-resistant bacteria. Further, the compounds of the present invention exhibit bacteriacidal activity.

The present invention comprises, in one aspect, antibacterial compounds of Formula I:

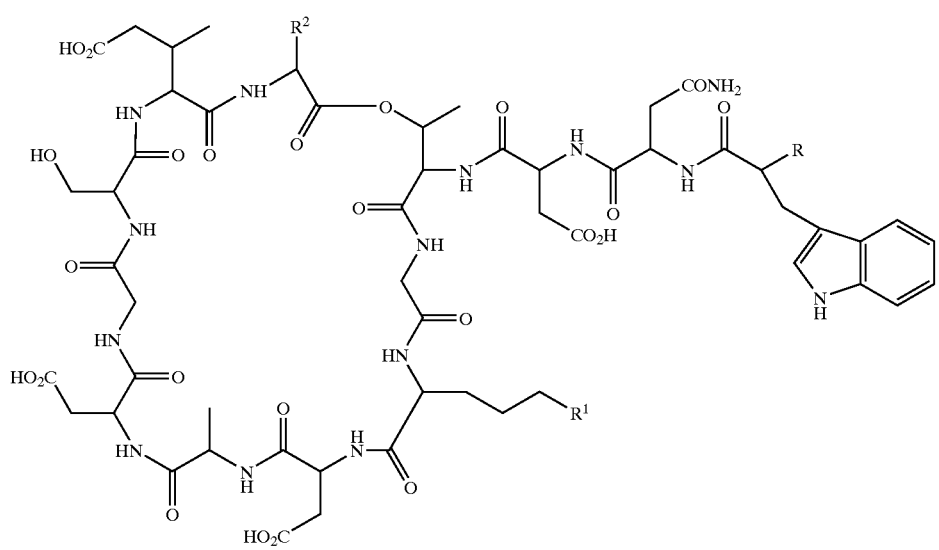

(I)

and salts thereof,
wherein R and $R^1$ are independently:

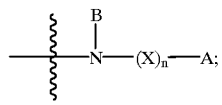

wherein X and X' are independently selected from C=O, C=S, C=NH, C=$NR^X$, S=O or $SO_2$;
wherein n is 0 or 1;
wherein $R^X$ is selected from alkyl, alkenyl, alkynyl, aryl, heteroaryl, cycloalkyl, heterocyclyl, hydroxyl, alkoxy, carboxy or carboalkoxy;
wherein B is $X'R^Y$, H, alkyl, alkenyl, alkynyl, aryl, heteroaryl, cycloalkyl or heterocyclyl;

wherein $R^Y$ is selected from hydrido, alkyl, alkenyl, alkynyl, aryl, heteroaryl, cycloalkyl, heterocyclyl or hydroxyl;

wherein A is H, $NH_2$, $NHR^A$, $NR^A R^B$, alkyl, alkenyl, alkynyl, alkoxy, aryloxy, aryl, heteroaryl, cycloalkyl, heterocyclyl;

wherein $R^A$ and $R^B$ are independently selected from alkyl, alkenyl, alkynyl, aryl, heteroaryl, cycloalkyl, heterocyclyl or carboalkoxy;

wherein when n is 0, then A is additionally selected from:

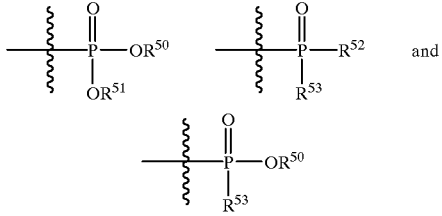

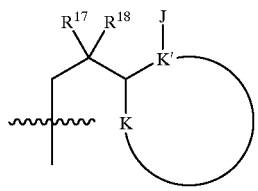

wherein each of $R^{50}$–$R^{53}$ is independently selected from $C_1$–$C_{15}$ alkyl;

alternatively, B and A together form a 5–7 membered heterocyclic or heteroaryl ring.

Wherein $R^2$ is

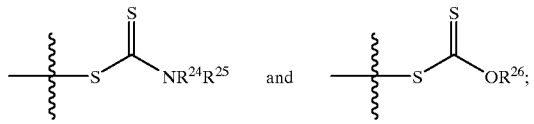

wherein K and K' together form a $C_3$–$C_7$ cycloalkyl or heterocyclyl ring or a $C_5$–$C_{10}$ aryl or heteroaryl ring;

wherein J is selected from the group consisting of hydrido, amino, $NHR^J$, $NR^J R^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

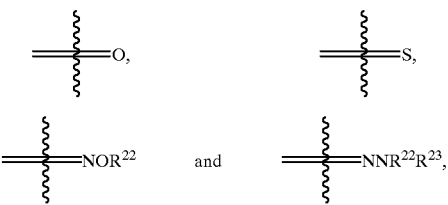

wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5–8 membered heterocyclyl ring;

wherein $R^J$ and $R^K$ are independently selected from alkyl, alkenyl, alkynyl, aryl, heteroaryl, cycloalkyl, heterocyclyl; or alternatively, wherein J, together with $R^{17}$, forms a 5–8 membered heterocyclyl or cycloalkyl ring; or alternatively, wherein J, together with both $R^{17}$ and $R^{18}$, forms a 5–8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and

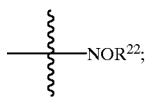

or wherein $R^{17}$ and $R^{18}$ taken together can form a group consisting of ketal, thioketal, wherein each of $R^{22}$ and $R^{23}$ is independently selected from the group consisting of hydrido and alkyl;

provided that when K and K' together form a phenyl ring and $R^{17}$ and $R^{18}$ taken together form C=O, then J is not $NH_2$, $C_4$–$C_{14}$ alkylidenyl, or $NHR^Q$, wherein $R^Q$ is $C_4$–$C_{14}$ unsubstituted alkyl, substituted or unsubstituted $C_2$–$C_{19}$ alkanoyl, unsubstituted $C_5$–$C_{19}$ alkenoyl, or a carboalkoxy.

In another embodiment, the invention also provides pharmaceutical compositions comprising compounds of Formula I and methods of use thereof.

In a further embodiment, the invention provides methods of making compounds of Formula I and pharmaceutical compositions thereof.

In a further embodiment, the invention provides compounds useful as intermediates for the preparation of compounds of Formula I.

In a still further embodiment, the invention provides methods of use of the compounds of Formula I to treat bacterial infections in humans.

DETAILED DESCRIPTION OF THE INVENTION

Definitions

Molecular terms, when used in this application, have their common meaning unless otherwise specified.

The term "hydrido" denotes a single hydrogen atom (H).

The term "acyl" is defined as a carbonyl radical attached to an alkyl, alkenyl, alkynyl, cycloalkyl, heterocycyl, aryl or heteroaryl group, examples including, without limitation, such radicals as acetyl and benzoyl.

The term "amino" denotes a nitrogen radical containing two substituents independently selected from the group consisting of hydrido, alkyl, cycloalkyl, carboalkoxy, heterocyclyl, aryl, heteroaryl and sulfonyl. Subsets of the term amino are (1) the term "unsubstituted amino" which denotes an $NH_2$ radical, (2) the term "mono substituted amino" which is defined as a nitrogen radical containing a hydrido group and a substituent group selected from alkyl, cycloalkyl, heterocyclyl, aryl, or heteroaryl, and (3) the term "disubstituted amino" which is defined as a nitrogen radical containing two substituent groups independently selected from, alkyl, cycloalkyl, heterocyclyl, aryl, and heteroaryl. Preferred mono substituted amino radicals are "lower mono substituted amino" radicals, whereby the substituent group is a lower alkyl group. Preferred disubstituted amino radicals are "lower disubstituted amino" radicals, whereby the substituent groups are lower alkyl.

The term "acyloxy" denotes an oxygen radical adjacent to an acyl group.

The term "acylamino" denotes a nitrogen radical adjacent to an acyl group.

The term "carboalkoxy" is defined as a carbonyl radical adjacent to an alkoxy or aryloxy group.

The term "carboxyamido" denotes a carbonyl radical adjacent to an amino group.

The term "halo" is defined as a bromo, chloro, fluoro or iodo radical.

The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about twenty carbon atoms unless otherwise specified. Preferred alkyl radicals are "lower alkyl" radicals having one to about five carbon atoms. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino, formyl and an amino acid side chain. Examples of alkyl groups include, without limitation, methyl, tert-butyl, isopropyl, and methoxymethyl. Subsets of the term alkyl are (1) "unsubstituted alkyl" which is defined as an alkyl group that bears no substituent groups (2) "substituted alkyl" which denotes an alkyl radical in which (a) one or more hydrogen atoms is replaced by a substituent group selected from acyl, acyloxy, carboalkoxy, carboxy, carboxyamido, cyano, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, N-acylaminosulfonyl or (b) two or more hydrogen atoms are each replaced by a substituent group independently selected from hydroxyl, carboxy, $C_1$–$C_3$ alkoxy, amino, acylamino, oxo or guanidino; and (3) the term "selected substituted alkyl" which denotes an alkyl radical in which (a) one proton is replaced by a group selected from hydroxyl, carboxy $C_1$–$C_3$ alkoxy, unsubstituted amino, acylamino, or acylamino phenyl or (b) one to three protons is replaced by a halo substituent.

The term "alkenyl" is defined as linear or branched radicals having two to about twenty carbon atoms, preferably three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration. Examples of alkenyl groups include, without limitation, ethylenyl or phenyl ethylenyl.

The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. An example of alkynyl group includes, without limitation, propynyl.

The term "aryl" or "aryl ring" denotes aromatic radicals in a single or fused carbocyclic ring system, having from five to fourteen ring members. In a preferred embodiment, the ring system has from six to ten ring members. One or more hydrogen atoms may also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of aryl groups include, without limitation, phenyl, naphthyl, biphenyl, terphenyl. Subsets of the term aryl are (1) the term "phenyl" which denotes a compound of the formula:

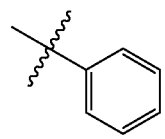

(2) the term "substituted phenyl" which is defined as a phenyl radical in which one or more protons are replaced by a substituent group selected from acyl, amino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino phenyl" denotes a phenyl radical in which one hydrogen atom is replaced by an acylamino group. One or more additional hydrogen atoms can also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

"Heteroaryl" or "heteroaryl ring" denotes an aromatic radical which contain one to four hetero atoms or hetero groups selected from O, N, S,

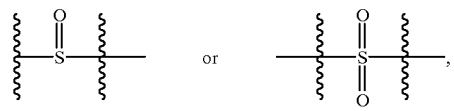

in a single or fused heterocyclic ring system, having from five to fifteen ring members. In a preferred embodiment, the heteroaryl ring system has from six to ten ring members. One or more hydrogen atoms may also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Subsets of the term heteroaryl are (1) the term "pyridinyl" which denotes compounds of the formula:

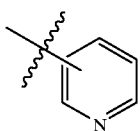

(2) the term "substituted pyridinyl" which is defined as a pyridinyl radical in which one or more protons is replaced by a substituent group selected from acyl, amino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino pyridinyl" which denotes a pyridinyl radical in which one hydrogen atom is replaced by an acylamino group, additionally, one or more additional hydrogen atoms can also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. One or more hydrogen atoms may also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopropyl, cyclobutyl, cyclohexyl, and cycloheptyl.

The term "heterocyclyl," "heterocyclic" or "heterocyclyl ring" is defined as a saturated or partially unsaturated ring containing one to four hetero atoms or hetero groups selected from O, N, NH,

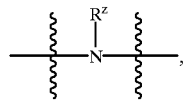

wherein $R^z$ is as defined for $R^x$,

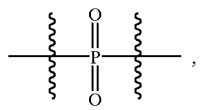

S,

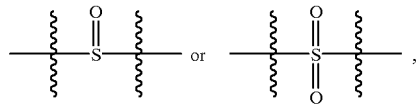

in a single or fused heterocyclic ring system having from three to twelve ring members. In a preferred embodiment, a heterocyclyl is a ring system having three to seven ring members. One or more hydrogen atoms may also be replaced by a substituent group selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a heterocyclyl group include, without limitation, morpholinyl, piperidinyl, and pyrrolidinyl.

The term "alkoxy" denotes oxy-containing radicals substituted with an alkyl, cycloalkyl or heterocyclyl group. Examples include, without limitation, methoxy, tert-butoxy, benzyloxy and cyclohexyloxy.

The term "aryloxy" denotes oxy-containing radicals substituted with an aryl or heteroaryl group. Examples include, without limitation, phenoxy.

The term "amino acid side chain" denotes any side chain (R group) from a naturally-occurring or a non-naturally occurring amino acid.

The term "sulfinyl" is defined as a tetravalent sulfur radical substituted with an oxo substituent and a second substituent selected from the group consisting of alkyl, cycloalkyl, heterocyclyl, aryl, or heteroaryl group.

The term "sulfonyl" is defined as a hexavalent sulfur radical substituted with two oxo substituents and a third substituent selected from alkyl, cycloalkyl, heterocyclyl aryl, or heteroaryl.

The term "carbamate amino protecting group" is defined as a recognized amino protecting group that when bound to an amino group forms a carbamate. Examples of carbamate amino protecting groups can be found in "Protective Groups in Organic Synthesis" by Theodora W. Greene, John Wiley and Sons, New York, 1981. Examples of carbamate amino protecting groups include benzyloxycarbonyl, t-butoxycarbonyl, t-amyloxycarbonyl, isobornyloxycarbonyl, adamantyloxycarbonyl, chlorobenzyloxycarbonyl, nitrobenzyloxycarbonyl or the like.

The salts of the compounds of the invention (preferably a compound of Formula I) include acid addition salts and base addition salts. In a preferred embodiment, the salt is a pharmaceutically acceptable salt of the compound of Formula I. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids include, without limitation, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention (preferably a compound of Formula I) by treating, for example, the compound of the invention (preferably a compound of Formula I) with the appropriate acid or base.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula I) can be utilized in the present invention as a single isomer or as a mixture of stereochemical isomeric forms. Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably at least 20%, more preferably at least 50% and most preferably at least 80% of the compound present in the mixture. In a preferred embodiment, the compound, a pharmaceutically acceptable salt thereof, or a pharmaceutical composition comprising the compound exhibits a detectable (i.e. statistically significant) antimicrobial activity when tested in conventional biological assays such as those described herein.

Lipopeptide Compounds

The invention provides a compound Formula (I):

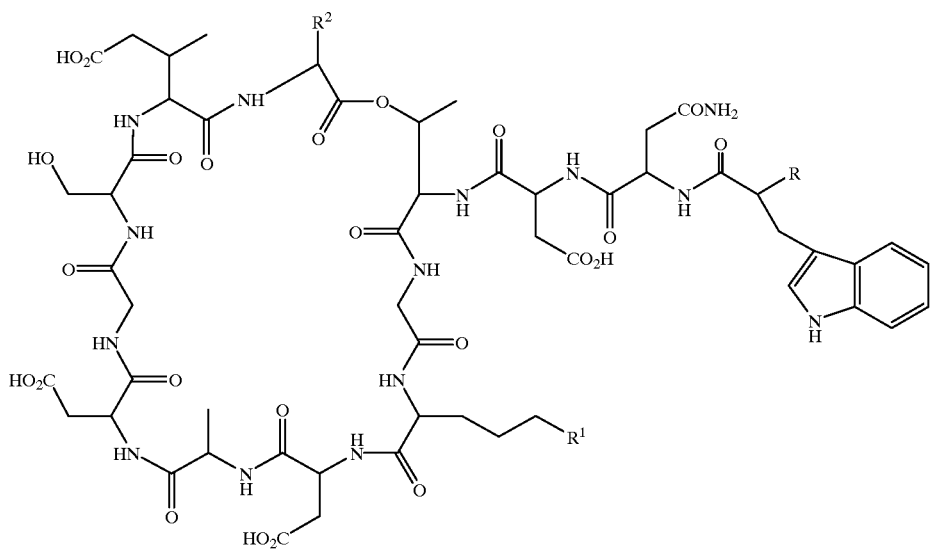

(I)

and salts thereof

Wherein R and $R^1$ are independently:

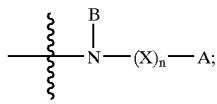

wherein X and X' are independently selected from C=O, C=S, C=NH, C=$NR^X$, S=O or $SO_2$;

wherein n is 0 or 1;

wherein $R^X$ is selected from alkyl, alkenyl, alkynyl, aryl, heteroaryl, cycloalkyl, heterocyclyl, hydroxyl, alkoxy, carboxy or carboalkoxy;

wherein B is $X'R^Y$, H, alkyl, alkenyl, alkynyl, aryl, heteroaryl, cycloalkyl or heterocyclyl;

wherein $R^Y$ is selected from hydrido, alkyl, alkenyl, alkynyl, aryl, heteroaryl, cycloalkyl, heterocyclyl or hydroxyl, wherein A is H, $NH_2$, $NHR^A$, $NR^AR^B$, alkyl, alkenyl, alkynyl, alkoxy, aryloxy, aryl, heteroaryl, cycloalkyl, heterocyclyl;

wherein $R^A$ and $R^B$ are independently selected from alkyl, alkenyl, alkynyl, aryl, heteroaryl, cycloalkyl, heterocyclyl or carboalkoxy;

wherein when n is 0, then A is additionally selected from:

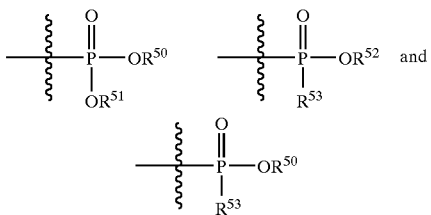

wherein each of $R^{50}$–$R^{53}$ is independently selected from $C_1$–$C_{15}$ alkyl;

alternatively, B and A together form a 5–7 membered heterocyclic or heteroaryl ring.

Wherein $R^2$ is

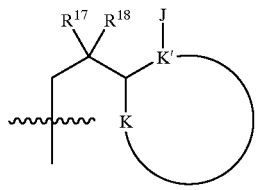

wherein K and K' together form a $C_3$–$C_7$ cycloalkyl or heterocyclyl ring or a $C_5$–$C_{10}$ aryl or heteroaryl ring, wherein J is selected from the group consisting of hydrido, amino, $NHR^J$, $NR^JR^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

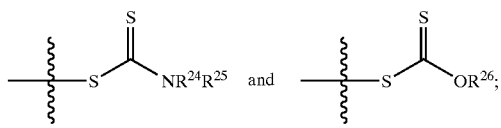

wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5–8 membered heterocyclyl ring;

wherein $R^J$ and $R^K$ are independently selected from alkyl, alkenyl, alkynyl, aryl, heteroaryl, cycloalkyl, heterocyclyl; or alternatively, wherein J, together with $R^{17}$, forms a 5–8 membered heterocyclyl or cycloalkyl ring; or alternatively, wherein J, together with both $R^{17}$ and $R^{18}$, forms a 5–8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and

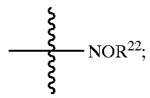

or wherein $R^{17}$ and $R^{18}$ taken together can form a group consisting of ketal, thioketal,

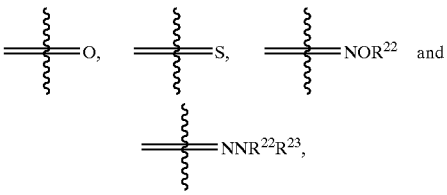

wherein each of $R^{22}$ and $R^{23}$ is independently selected from the group consisting of hydrido and alkyl;

provided that when K and K' together form a phenyl ring and $R^{17}$ and $R^{18}$ taken together form C=O, then J is not $NH_2$, $C_4$–$C_{14}$ alkylidenyl, or $NHR^Q$, wherein $R^Q$ is $C_4$–$C_{14}$ unsubstituted alkyl, substituted or unsubstituted $C_2$–$C_{19}$ alkanoyl, unsubstituted $C_5$–$C_{19}$ alkenoyl, or a carboalkoxy.

In a preferred embodiment of the invention, R is selected from

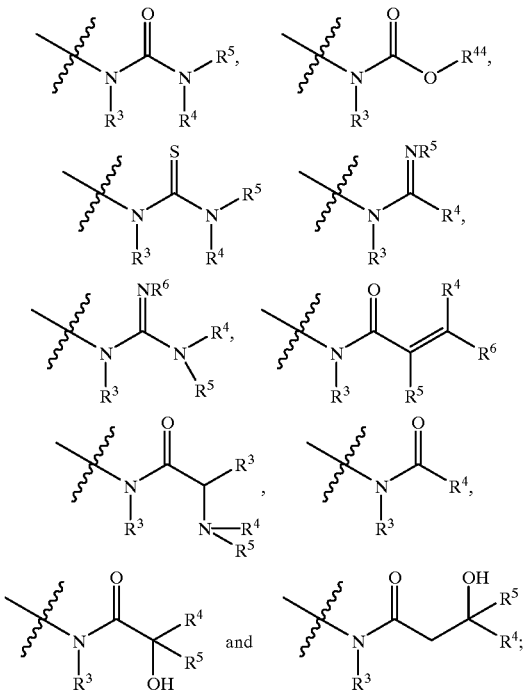

wherein each of $R^3$, $R^4$ $R^5$, and $R^6$ is independently selected from the group consisting of hydrido, alkyl, aryl, heterocyclyl and heteroaryl, and wherein $R^{44}$ is selected from the group consisting of alkyl, aryl, heterocyclyl and heteroaryl.

In a more preferred embodiment of the invention R is selected from

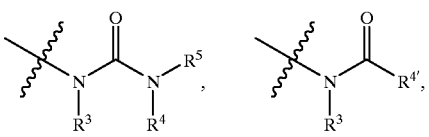

-continued

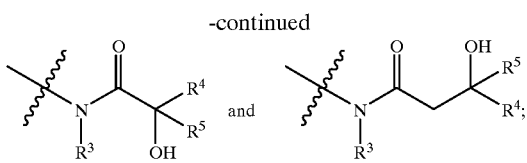

wherein $R^{41}$ is selected from the group consisting of alkyl, aryl-substituted alkyl, substituted phenyl, heteroaryl, heterocyclyl, optionally substituted $(C_8-C_{14})$-straight chain alkyl and

wherein $R^7$ is an alkyl group.

In an even more preferred embodiment of the invention, R is

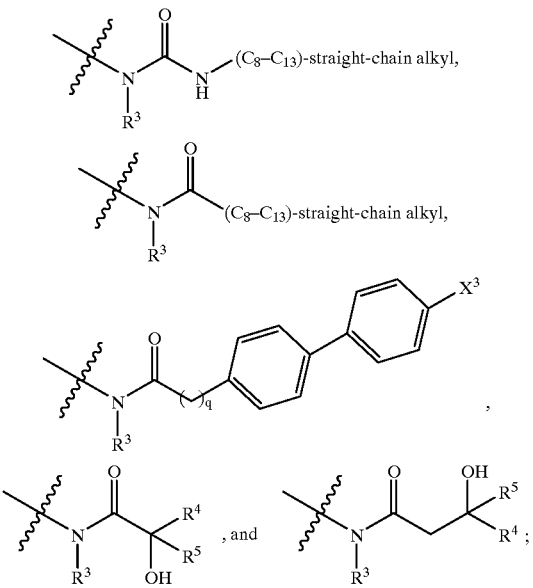

wherein $X^3$ is chloro or trifluoromethyl and wherein q is 0 or 1.

In a preferred embodiment of the invention, $R^1$ is selected from the group consisting of:

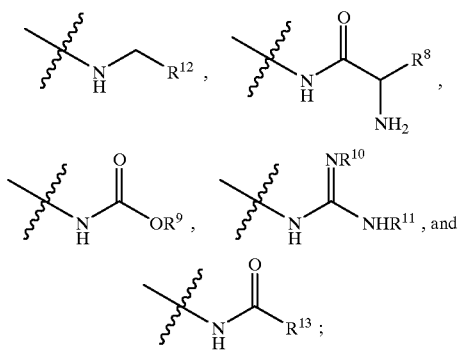

wherein $R^8$ is selected from an amino acid side chain, wherein said amino acid side chain may be one that is naturally occurring or one that is not naturally occurring, wherein each of $R^9$, $R^{10}$ and $R^{11}$ is selected from hydrido, alkyl, aryl, heterocyclyl and heteroaryl; wherein $R^{12}$ is selected from the group consisting of heterocyclyl, heteroaryl, aryl, and alkyl and wherein $R^{13}$ is selected from $(C_1-C_3)$-alkyl and aryl.

In a more preferred embodiment of the invention, $R^1$ is selected from the group consisting of

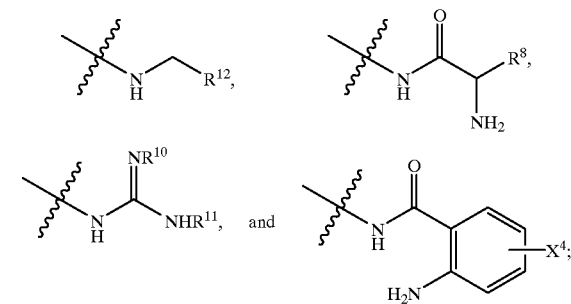

wherein $R^8$ is selected from tryptophan side chain and lysine side chain; wherein each of $R^{10}$ and $R^{11}$ is independently selected from hydrido and alkyl; wherein $R^{12}$ is selected from imidazolyl, N-methylimidazolyl, indolyl, quinolinyl, benzyloxybenzyl, and benzylpiperidenylbenzyl; and wherein $X^4$ is selected from fluoro and trifluoromethyl.

In a preferred embodiment of $R^2$, J is selected from the group consisting of hydrido, amino, azido and

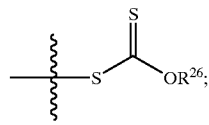

wherein $R^{17}$ and $R^{18}$ taken together form a group selected from the group consisting of ketal,

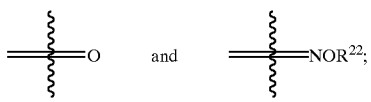

alternatively, $R^{17}$ is hydroxyl when $R^{18}$ is hydrido. Alternatively, wherein J, together with $R^{17}$, forms a heterocyclyl ring.

In a more preferred embodiment of the invention, $R^2$ is selected from

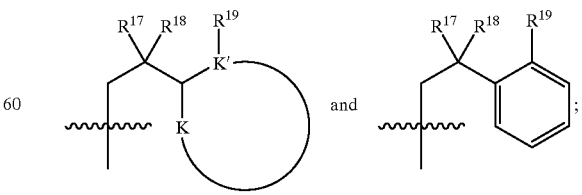

wherein $R^{17}$ and $R^{18}$ taken together form a group selected from

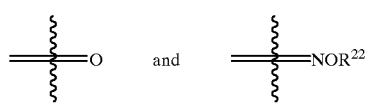
wherein $R^{22}$ is selected from the group consisting of H and alkyl; wherein $R^{19}$ is selected from the group consisting of hydrido, amino, azido and
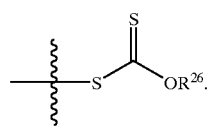
Another aspect of the present invention provides compounds of formula (I), wherein R is selected from NHCO($C_6$–$C_{14}$ alkyl)$CH_3$, and $R_1$ and $R_2$ are selected from Table A. Preferably, R is selected from NHCO[$(CH_2)_{6-14}$]-$CH_3$.

TABLE A-continued

| R¹ | R² |
|---|---|
| (tryptophan-amide group with NH₂) | (phenyl ketone group) |
| NH₂ | (dioxolane with 2-azidophenyl group) |
| NH₂ | (CH(OH) with 2-azidophenyl group) |

Table I provides exemplary compounds of Formula I:

TABLE 1

| Cpd # | R | R¹ | R² | Mass Spec | Synth Ex. # |
|---|---|---|---|---|---|
| 1 | NHCO(CH₂)₈CH₃ | NH₂ | (2-azidophenyl ketone) | 1646.7 | 2 |
| 2 | NHCO(CH₂)₈CH₃ | NH₂ | (2-(S-C(=S)NEt₂)phenyl ketone) | 1752.9 | 1 |
| 3 | NHCO(CH₂)₈CH₃ | NH₂ | (2-(S-C(=S)OEt)phenyl ketone) | 1725.9 | 1 |
| 4 | NHCO(CH₂)₈CH₃ | NH₂ | (2-(S-C(=S)-pyrrolidinyl)phenyl ketone) | 1750.9 | 1 |
| 5 | NHCO(CH₂)₈CH₃ | NH₂ | (phenyl ketone) | 1605.7 | 3 |

TABLE 1-continued

| Cpd # | R | R¹ | R² | Mass Spec | Synth Ex. # |
|---|---|---|---|---|---|
| 6 | NHCO(CH$_2$)$_8$CH$_3$ | NH$_2$ | (CH$_2$-C(=NOH)-phenyl) | 1622.7 | 3 |
| 7 | NHCO(CH$_2$)$_8$CH$_3$ | NH$_2$ | (CH$_2$-C(=NOH)-(2-N$_3$-phenyl)) | 1661.7 | 2 |
| 8 | NHCO(CH$_2$)$_8$CH$_3$ | NH$_2$ | (CH$_2$-C(=NOCH$_3$)-phenyl) | 1634.7 | 3 |
| 9 | NHCO(CH$_2$)$_8$CH$_3$ | NH$_2$ | (CH$_2$-indazol-3-yl) | 1617.7 | 4 |
| 10 | NHCO(CH$_2$)$_8$CH$_3$ | 2-(NHCH$_3$)benzamide-NH- | (CH$_2$-C(=O)-(2-N$_3$-phenyl)) | 1779.8 | 2 |
| 11 | NHCO(CH$_2$)$_8$CH$_3$ | biotinyl-NH- | (CH$_2$-C(=O)-(2-N$_3$-phenyl)) | 1872 | 2 |
| 12 | NHCO(CH$_2$)$_8$CH$_3$ | Tyr-NH- | (CH$_2$-C(=O)-(2-N$_3$-phenyl)) | 1809.9 | 2 |
| 13 | NHCO(CH$_2$)$_8$CH$_3$ | NH$_2$ | (CH$_2$-C(=NOCH$_3$)-(2-N$_3$-phenyl)) | 1677 | 2 |

TABLE 1-continued

| Cpd # | R | R¹ | R² | Mass Spec | Synth Ex. # |
|---|---|---|---|---|---|
| 14 | NHCO(CH$_2$)$_8$CH$_3$ | (tryptophan-amide group) | (benzoyl group) | 1791.9 | 3a |
| 15 | NHCO(CH$_2$)$_8$CH$_3$ | NH$_2$ | (2-azidophenyl dioxolane group) | 1690.7 | 2a |
| 16 | NHCO(CH$_2$)$_8$CH$_3$ | NH$_2$ | (2-azidophenyl hydroxyethyl group) | 1648.7 | 2b |

Preferred compounds of Formula I are Compound 3 and Compound 5.

Lipopeptide Intermediates

The present invention also provides compounds that are particularly useful as intermediates for the preparation of the compounds of Formula I. These compounds may also have antibacterial properties, as discussed above. In one aspect of the invention, compounds of Formula II are provided:

wherein $R^{14}$ is selected from the group consisting of

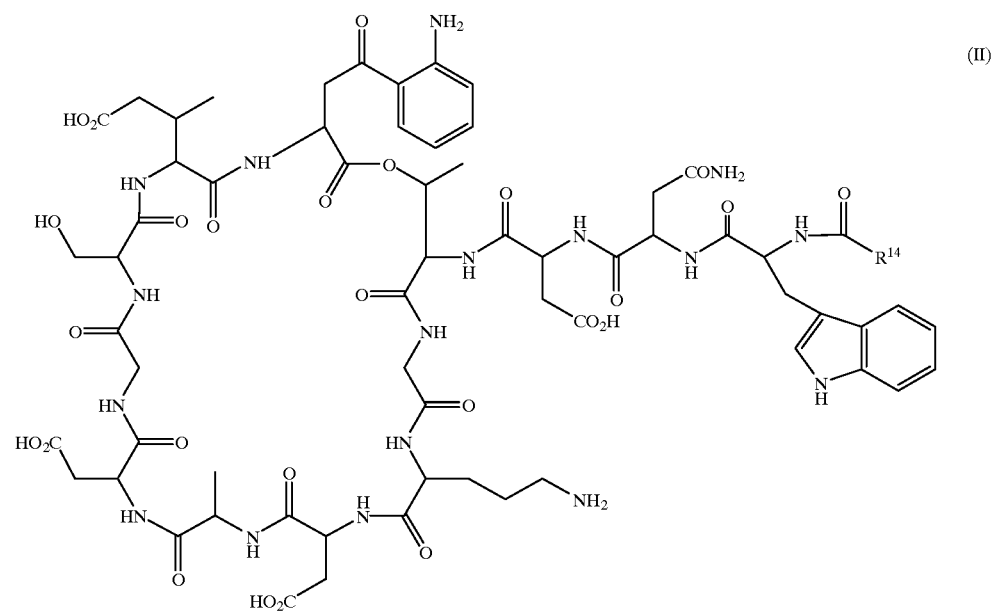

(II)

-continued

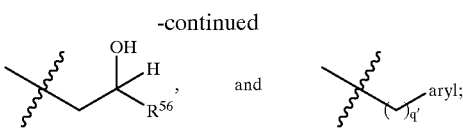

wherein $R^{56}$ is an optionally substituted straight-chain $C_8$–$C_{14}$ alkyl group and wherein q' is 0–3.

In another aspect of the invention, compounds of Formula III are provided as useful intermediates for the preparation of compounds of Formula I and/or as antibacterial compounds:

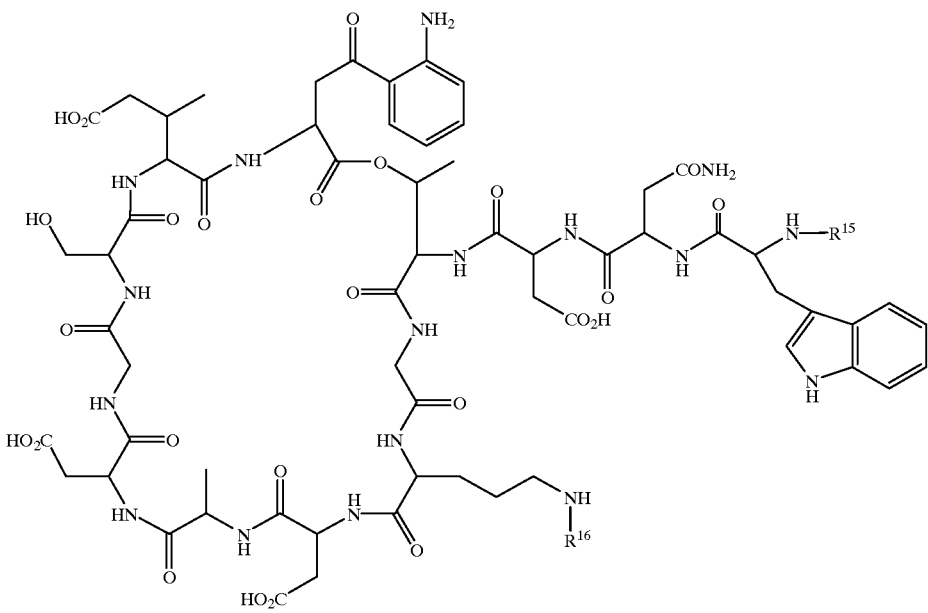

(III)

wherein $R^{15}$ is selected from hydrido and an carbamate amino protecting group, preferably a tert-butoxycarbonyl group; wherein $R^{16}$ is selected from the group consisting of

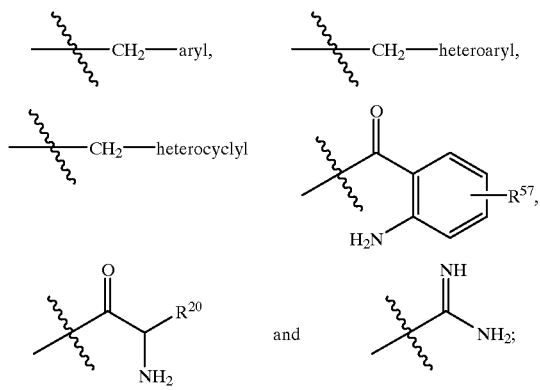

wherein $R^{57}$ is a halo or halo substituted alkyl group, preferably a fluoro or trifluoromethyl group; wherein, $R^{20}$ is an amino acid side chain, preferably a lysine or tryptophan side chain.

Lipopeptide Compound Pharmaceutical Compositions and Methods of Use Thereof

Another object of the instant invention is to provide lipopeptide compounds or salts thereof, as well as pharmaceutical compositions or formulations comprising lipopeptide compounds or its salts.

Lipopeptide compounds, or pharmaceutically acceptable salts thereof, can be formulated for oral, intravenous, intramuscular, subcutaneous or parenteral administration for the therapeutic or prophylactic treatment of diseases, particularly bacterial infections. For oral or parenteral administration, lipopeptide compounds of this invention can be mixed with conventional pharmaceutical carriers and excipients and used in the form of tablets, capsules, elixirs, suspensions, syrups, wafers and the like. The compositions comprising a compound of this invention will contain from about 0.1 to about 99% by weight of the active compound, and more generally from about 10 to about 30%.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. No. 4,452,775 (issued to Kent), U.S. Pat. No. 5,239,660 (issued to Leonard), U.S. Pat. No. 3,854,480 (issued to Zaffaroni).

The pharmaceutically-acceptable compositions of the present invention comprise one or more compounds of the invention (preferably compounds of Formula I) in association with one or more nontoxic, pharmaceutically-acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc, disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propylpara-hydroxybenzoate, propylene glycol, sorbitol, or sorbic acid.

For intravenous (IV) use, a lipopeptide compound according to the invention can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of a lipopeptide compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular or parental formulation of a lipopeptide compound may be administered as a bolus or by slow infusion. A bolus is a dose that is administered in less than 30 minutes. In a preferred embodiment, a bolus is administered in less than 15 or less than 10 minutes. In a more preferred embodiment, a bolus is administered in less than 5 minutes. In an even more preferred embodiment, a bolus is administered in one minute or less. An infusion is a dose that is administered at a rate of 30 minutes or greater. In a preferred embodiment, the infusion is one hour or greater. In another embodiment, the infusion is substantially constant.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery. In another embodiment, the unit dosage form of the compound can be a solution of the compound or preferably a salt thereof in a suitable diluent in sterile, hermetically sealed ampoules or sterile syringes. The concentration of the compound in the unit dosage may vary, e.g. from about 1 percent to about 50 percent, depending on the compound used and its solubility and the dose desired by the physician. If the compositions contain dosage units, each dosage unit preferably contains from 1–500 mg of the active material. For adult human treatment, the dosage employed preferably ranges from 5 mg to 10 g, per day, depending on the route and frequency of administration.

In another aspect, the invention provides a method for inhibiting the growth of microorganisms, preferably bacteria, comprising contacting said organisms with a compound of the invention, preferably a compound of Formula I, under conditions which permit entry of the compound into said organism and into said microorganism. Such conditions are known to one skilled in the art and are exemplified in the Examples. This method involves contacting a microbial cell with a therapeutically-effective amount of compound(s) of the invention, preferably compound(s) of Formula I, in vivo or in vitro.

According to this aspect of the invention, the novel compositions disclosed herein are placed in a pharmaceutically acceptable carrier and are delivered to a recipient subject (preferably a human) in accordance with known methods of drug delivery. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention (preferably compounds of Formula I) for the agents used in the art-recognized protocols.

In one embodiment, the invention provides a method for treating an infection, especially those caused by gram-positive bacteria, in a subject with a therapeutically-effective amount of a lipopeptide compound according to Formula I. Exemplary procedures for delivering an antibacterial agent are described in U.S. Pat. No. 5,041,567, issued to Rogers and in PCT patent application number EP94/02552 (publication no. WO 95/05384), the entire contents of which documents are incorporated in their entirety herein by reference. As used herein the phrase "therapeutically-effective amount" means an amount of a compound of the present invention that prevents the onset, alleviates the symptoms, or stops the progression of a bacterial infection. The term "treating" is defined as administering, to a subject, a therapeutically-effective amount of a compound of the invention (preferably a compound of Formula I) both to prevent the occurrence of an infection and to control or eliminate an infection. The term "subject", as described herein, is defined as a mammal, a plant or a cell culture. In a preferred embodiment, a subject is a human or other animal patient in need of lipopeptide compound treatment.

The method comprises administering to the subject an effective dose of a compound of this invention An effective dose is generally between about 0.1 and about 100 mg/kg of a lipopeptide compound of Formula I or a pharmaceutically acceptable salt thereof. A preferred dose is from about 0.1 to about 50 mg/kg of a lipopeptide compound of Formula I or a pharmaceutically acceptable salt thereof. A more preferred dose is from about 1 to 25 mg/kg of a lipopeptide compound of Formula I or a pharmaceutically acceptable salt thereof. An effective dose for cell culture is usually between 0.1 and 1000 µg/mL, more preferably between 0.1 and 200 µg/mL.

The compound of Formula I can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. A method of administration to a patient of daptomycin, another member of the lipopeptide compound class, is disclosed in U.S. Ser. No. 09/406,568, filed Sep. 24, 1999, which claims the benefit of U.S. Provisional Application No. 60/101,828, filed Sep. 25, 1998, and No. 60/125,750, filed Mar. 24, 1999.

A lipopeptide compound according to this invention may also be administered in the diet or feed of a patient or animal. If administered as part of a total dietary intake, the amount of compound employed can be less than 1% by weight of the diet and preferably no more than 0.5% by weight. The diet for animals can be normal foodstuffs to which the compound can be added or it can be added to a premix.

The methods of the present invention comprise administering a lipopeptide compound of Formula I or a pharmaceutical composition thereof to a subject in need thereof in an amount that is efficacious in reducing or eliminating the bacterial infection. The compound may be administered orally, parenterally, by inhalation, topically, rectally, nasally, buccally, vaginally, or by an implanted reservoir, external pump or catheter. The compound may be prepared for opthalmic or aerosolized uses. The compounds of the present invention can be administered as an aerosol for the treatment of pneumonia or other lung-based infections. A preferred aerosol delivery vehicle is an anhydrous or dry powder inhaler. Lipopeptide compounds of Formula I or a pharmaceutical composition thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In a preferred embodiment, lipopeptide compounds are administered intravenously, subcutaneously or orally. In a preferred embodiment for administering a lipopeptide compound according to Formula I to a cell culture, the compound may be administered in a nutrient medium.

The method of the instant invention may be used to treat a subject having a bacterial infection in which the infection is caused or exacerbated by any type of bacteria, particularly gram-positive bacteria. In one embodiment, a lipopeptide compound or a pharmaceutical composition thereof is administered to a patient according to the methods of this invention. In a preferred embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), penicillin-susceptible and penicillin-resistant streptococci (including *Streptococcus pneumoniae, S. pyogenes, S. agalactiae, S. avium, S. bovis, S. lactis, S. sangius* and Streptococci Group C, Streptococci Group G and viridans streptococci), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Haemophilus influenzae, Listeria monocytogenes, Corynebacterium jeikeium*, Bifidobacterium spp., *Eubacterium aerofaciens, E. lentum, Lactobacillus acidophilus, L. casei, L. plantarum*, Lactococcus spp., Leuconostoc spp., Pediococcus, *Peptostreptococcus anaerobius, P. asaccarolyticus, P. magnus, P. micros, P. prevotii, P. productus, Propionibacterium acnes*, Actinomyces spp., Moraxella spp. (including *M. catarrhalis*) and Escherichia spp. (including *E. coli*).

In a preferred embodiment, the antibacterial activity of lipopeptide compounds of Formula I against classically "resistant" strains is comparable to that against classically "susceptible" strains in in vitro experiments. In another preferred embodiment, the minimum inhibitory concentration (MNC) value for lipopeptide compounds according to this invention against susceptible strains is typically the same or lower than that of vancomycin. Thus, in a preferred embodiment, a lipopeptide compound of this invention or a pharmaceutical composition thereof is administered according to the methods of this invention to a patient who exhibits a bacterial infection that is resistant to other compounds, including vancomycin or daptomycin. In addition, unlike glycopeptide antibiotics, lipopeptide compounds exhibits rapid, concentration-dependent bactericidal activity against gram-positive organisms. Thus, in a preferred embodiment, a lipopeptide compound according to this invention or a pharmaceutical composition thereof is administered according to the methods of this invention to a patient in need of rapidly acting antibiotic therapy.

The method of the instant invention may be used for any bacterial infection of any organ or tissue in the body. In a preferred embodiment, the bacterial infection is caused by gram-positive bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *S. pneumoniae* or *H. influenzae*. The method of the invention also may be used to treat mixed infections that comprise different types of gram-positive bacteria, or which comprise both gram-positive and gram-negative bacteria. These types of infections include intra-abdominal infections and obstetrical/gynecological infections. The method of the invention also may be used to treat an infection including, without limitation, endocarditis, nephritis, septic arthritis, intra-abdominal sepsis, bone and joint infections and osteomyelitis. In a preferred embodiment, any of the above-described diseases may be treated using lipopeptide compounds according to this invention or pharmaceutical compositions thereof The method of the instant invention may also be practiced while concurrently administering one or more other antimicrobial agents, such as antibacterial agents (antibiotics) or antifungal agents. In one aspect, the method may be practiced by administering more than one lipopeptide compounds according to this invention. In another embodiment, the method may be practiced by administering a lipopeptide compound according to this invention with another lipopeptide compound, such as daptomycin.

Antibacterial agents and classes thereof that maybe co-administered with a compound of the present invention include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomicins, glycopeptide, glycylcycline, ketolides, oxazolidinone; imipenen, amikacin, netilmicin, fosfomycin, gentamicin, ceftriaxone, Ziracin, LY 333328, CL 331002, Linezolid, Synercid, Aztreonam, Metronidazole, Epiroprim, OCA-983, GV-143253, Sanfetrinem sodium, CS-834, Biapenem, A-99058.1, A-165600, A-179796, KA 159, Dynemicin A, DX8739, DU 6681; Cefluprenam, ER 35786, Cefoselis, Sanfetrineni celexctil, HGP-31, Cefpirome, HMR-3647, RU-59863, Mersacidin, KP 736, Rifalazil; Kosan, AM 1732, MEN 10700, Lenapenem, BC 2502A, NE-1530, PR 39(L-arginyl-L-arginyl-L-arginyl-L-prolyl-L-arginyl-L-prolyl-L-prolyl-L-tyrosyl-L-leucyl-L-prolyl-L-arginyl-L—prolyl-L-arginyl-L-prolyl-L-prolyl-L-prolyl-L-phenylalanyl-L-phenylalanyl-L-prolyl-L-prolyl-L-arginyl-L-leucyl-L-prolyl-L-prolyl-L—arginyl-L-isoleucyl-L-prolyl-L-prolylglycyl-L-phenylalanyl-L-prolyl-L-prolyl-L-arginyl—L-phenylalanyl-L-prolyl-L-prolyl-L-arginyl-L-phenylalanyl-L-prolinamide-[SEQ. ID NO: 1]), K130, OPC 20000, OPC 2045, Veneprim, PD 138312, PD 140248, CP 111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamet pivoxil, and T 3811.

In a preferred embodiment, antibacterial agents that may be co-administered with a compound according to this invention include, without limitation, imipenen, amikacin, netilmicin, fosfomycin, gentamicin, ceftriaxone, teicoplanin, Ziracin, LY 333328, CL 331002, HMR 3647, Linezolid, Synercid, Aztreonam, and Metronidazole.

Antifungal agents that may be co-administered with a compound according to this invention include, without limitation, Caspofungen, Voriconazole, Sertaconazole, IB-367, FK-463, LY-303366, Sch-56592, Sitafloxacin, DB-289 polyenes, such as Amphotericin, Nystatin, Primaricin; azoles, such as Fluconazole, Itraconazole, and Ketoconazole; allylamines, such as Naftifine and Terbinafine; and anti-metabolites such as Flucytosine. Other antifungal agents include without limitation, those disclosed in Fostel et al., Drug Discovery Today 5:25–32 (2000), herein incorporated by reference. Fostel et al. disclose antifungal compounds including Corynecandin, Mer-WF3010, Fusacandins, Artrichitin/LL 15G256γ, Sordarins, Cispentacin, Azoxybacillin, Aureobasidin and Khafrefungin.

Lipopeptide compounds may be administered according to this method until the bacterial infection is eradicated or reduced. In one embodiment, a lipopeptide compound is administered for a period of time from 3 days to 6 months. In a preferred embodiment, a lipopeptide compound is administered for 7 to 56 days. In a more preferred embodiment, a lipopeptide compound is administered for 7 to 28 days. In an even more preferred embodiment, a lipopeptide compound is administered for 7 to 14 days. Lipopeptide compounds may be administered for a longer or shorter time period if it is so desired.

General Procedures for Lipopeptide Compound Synthesis

Lipopeptide compounds of Formula I may be produced as described below. The lipopeptide compounds of the instant invention may be produced semi-synthetically using daptomycin as a starting point or may be produced by a total synthesis approach.

For the semi-synthetic approach according to the present invention, daptomycin may be prepared by any method known in the art. See, e.g., U.S. Pat. Nos. 4,885,243 and 4,874,843. Daptomycin may be used in its acylated state or it may be deacylated prior to its use as described herein. Daptomycin may be deacylated using *Actinoplanes utahensis* as described in U.S. Pat. No. 4,482,487. Alternatively, daptomycin may be deacylated as follows:

Daptomycin (5.0 g) was dissolved in water (25 ml) and adjusted to pH 9 with 5M sodium hydroxide. Ditert-butyldicarbonate (1.5 g) was added and the mixture was adjusted to maintain pH 9 with 5 M sodium hydroxide until the reaction was complete (4 hours). The pH was adjusted to 7 and the mixture was loaded onto a Bondesil 40μ C8 resin column. The column was washed with water and the product was eluted from the column with methanol. Evaporation of the methanol gave BOC-protected daptomycin as a yellow powder.

A preparation of deacylase enzyme was produced from recombinant *Streptomyces lividans*, which expresses the *Actinoplanes utahensis* deacylase enzyme. The enzyme in ethylene glycol (400 μl) was added to BOC-protected daptomycin (1 g) in water (100 ml) at pH 7–8. After incubation for 72 hours, the mixture was loaded on a Bondesil 40μ C8 resin column. The column was washed with water and the product was eluted from the column with 10% acetonitrile in water. The product was evaporated to give deacylated BOC-protected daptomycin as a yellow powder.

Kynurenine Derivatives

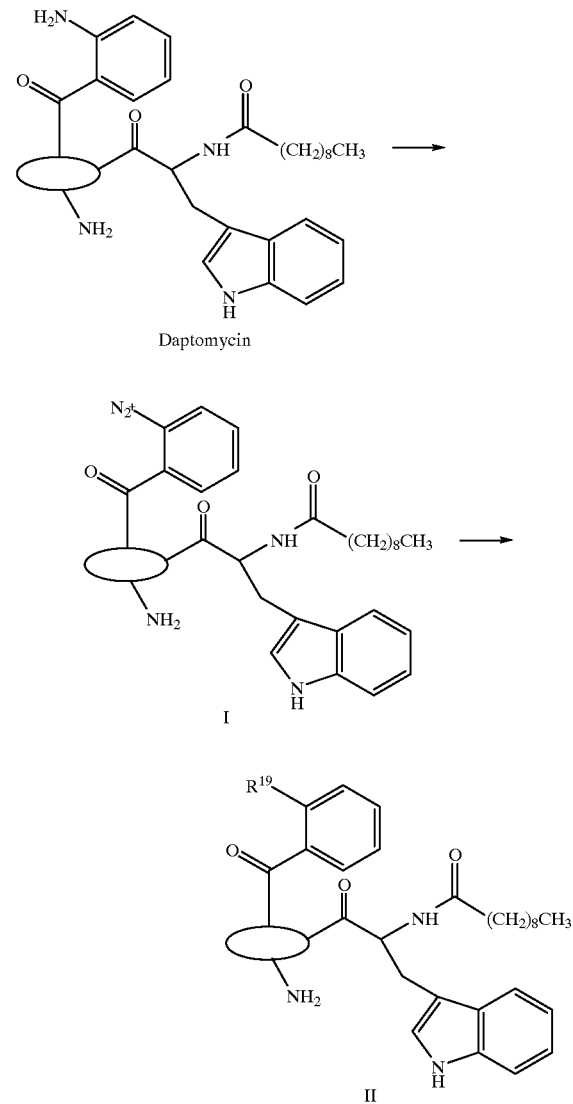

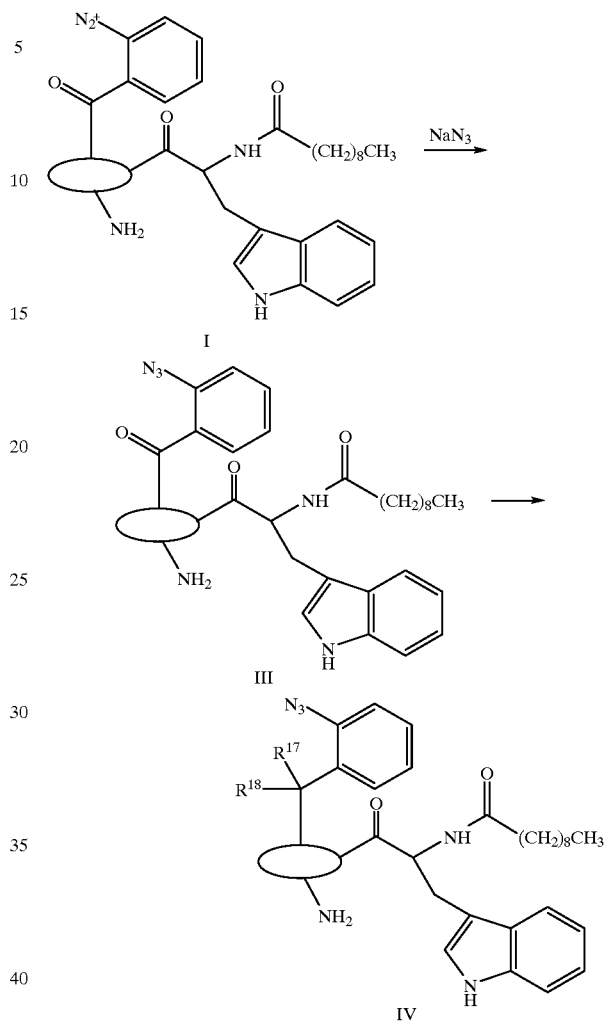

Daptomycin can be converted into analogs bearing modifications at the $R^2$ position by converting the aromatic amino group to the diazonium salt compound I with reagents such as sodium nitrite/hydrochloric acid or isoamylnitrite. Using chemistry known to those skilled in the art and following the teachings of the disclosure, the diazonium group can then be displaced by reagents such as sodium azide, potassium ethylxanthate or copper chloride to yield derivative compounds II, wherein $R^{19}$ is as previously defined.

Additionally, compound I can be converted to the azide compound III by reaction with an azide source, typically sodium azide. Modifications to the ketone group can then be undertaken using chemistry known to those having ordinary skill in the art, such as reduction, oxime formation, ketalization conversion to a leaving group and displacement to give compounds of formula IV, wherein $R^{17}$ and $R^{18}$ are as previously defined.

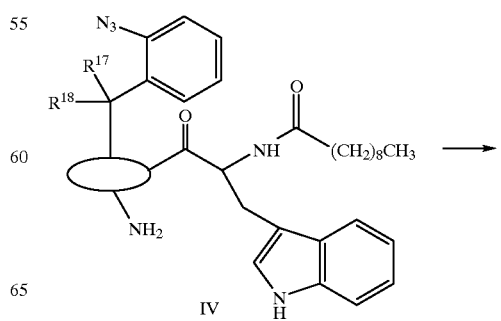

33

-continued

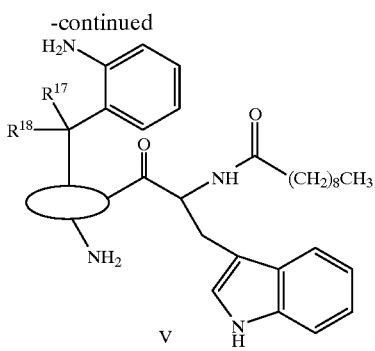

V

Compound IV may also be converted to compound V by reducing the azide group to the amine using chemistry known to those having ordinary skill in the art, and following the teachings of the disclosure, such as reaction with triphenyl phosphine and water, or reducing agents such as sodium borohydride wherein $R^{17}$ and $R^{18}$ are as previously defined.

Scheme 4

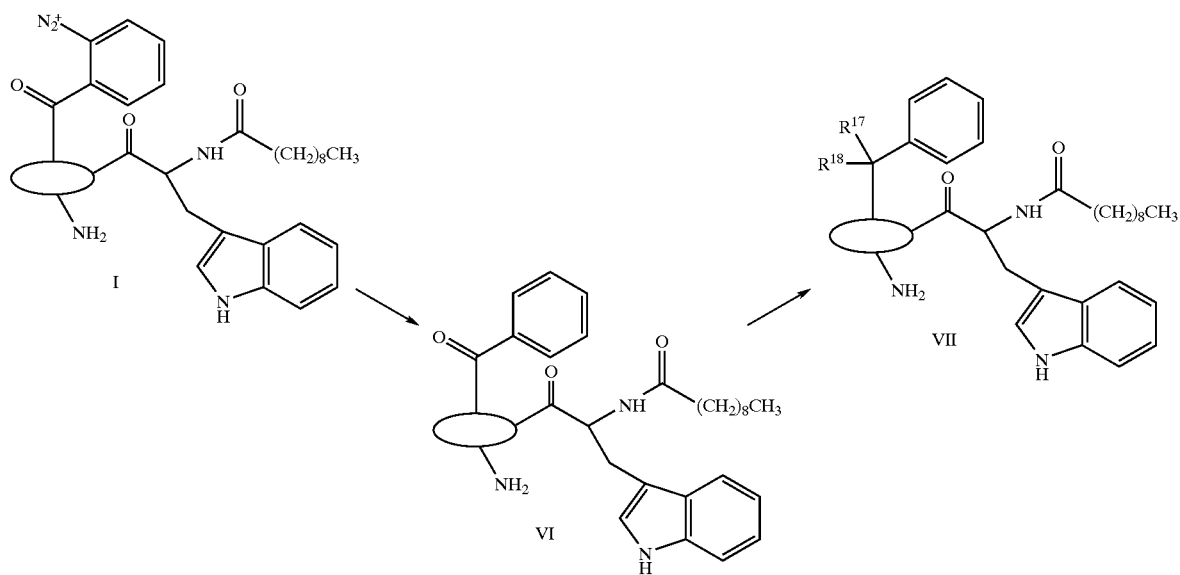

Additionally compound I can be converted into compound VI by reduction with hypophosphorus acid. Modifications to the ketone group can then be undertaken using chemistry known to those having ordinary skill in the art similar to those used in scheme 2, wherein $R^{17}$ and $R^{18}$ are as previously defined.

34

Ornithine Derivatives

Scheme 1

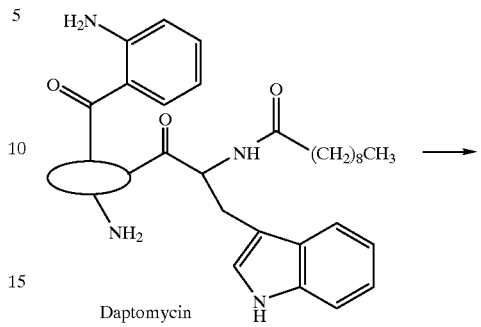

Daptomycin

-continued

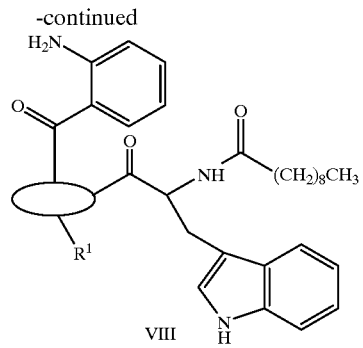

VIII

Daptomycin can be converted into analogs bearing modifications at the $R^1$ position by treating the aromatic amino group of the ornithine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound VIII, wherein $R^1$ is as previously defined.

Tryptophan Amine Derivatives

Scheme 1

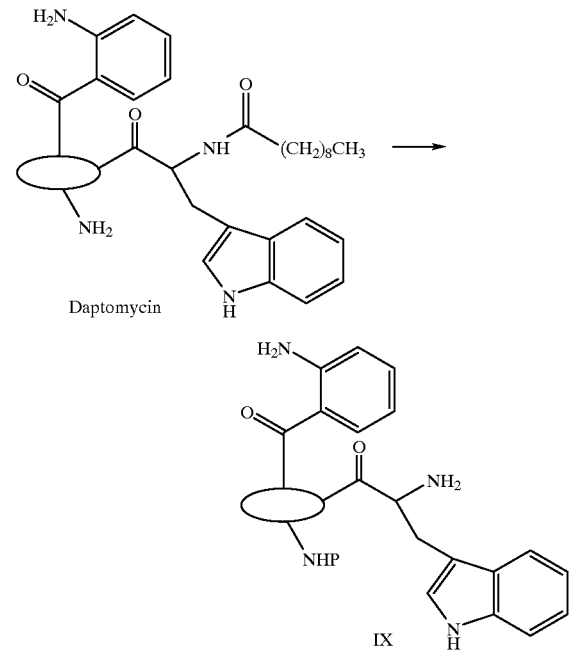

Daptomycin can be converted into compound IX by first protecting the ornithine amine with an appropriate amino protecting group (P) known to those skilled in the art and following the teachings of the disclosure. The decyl side chain on the tryptophan is then removed using an enzyme capable of deacylating daptomycin, such as that described above.

Scheme 2

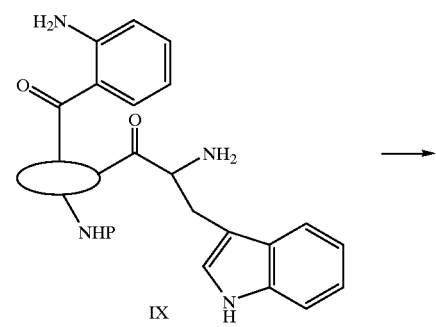

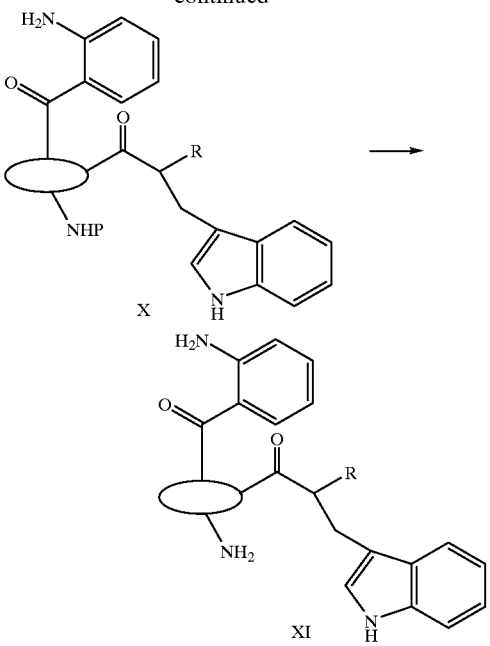

Compound IX can be modified at the tryptophan amine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound X. Compound X can be deprotected to give compound XI according to procedures known to those skilled in the art following the disclosure of this invention, wherein R is as previously defined.

The above modifications to the ornithine amine $R^1$, tryptophan amine R or kynurenine side chain $R^2$ may be independently combined to yield additional compounds that are modified at up to all three sites. In order to achieve these modifications, it may be necessary to protect certain functionalities in the molecule. Protecting these functionalities should be within the expertise of one skilled in the art following the disclosure of this invention. See, e.g., Greene, supra.

Solid Support Synthesis of Lipopeptide Compounds

In an alternative embodiment of the invention, the lipopeptide compounds of Formula I may be synthesized on a solid support as outlined below. In step 1, a suitably-N-protected-βMeGlu(OH)—OAllyl ester is coupled to a suitable resin to give Compound XII. Deprotection of the amino group of Compound XII, followed by coupling of the amino group with a suitably protected seryl derivative (A1) gives Compound XIII, wherein P is a suitable protecting group. This peptide coupling process, i.e., deprotection of the alpha-amino group, followed by coupling to a suitably protected amino acid, is repeated until the desired number of amino acids have been coupled to the resin. In the scheme shown below, eleven amino acids have been coupled to give Compound XIV. Addition of an activated R group, R*, is added to Compound XIV to give Compound XV. In step 4, Compound XV is cyclized to give Compound XVI. Subsequently, in step 5, Compound XVI is removed from the resin to give the lipopeptide Compound XVII.

Synthetic Scheme for Total Synthesis of Lipopeptide Compounds
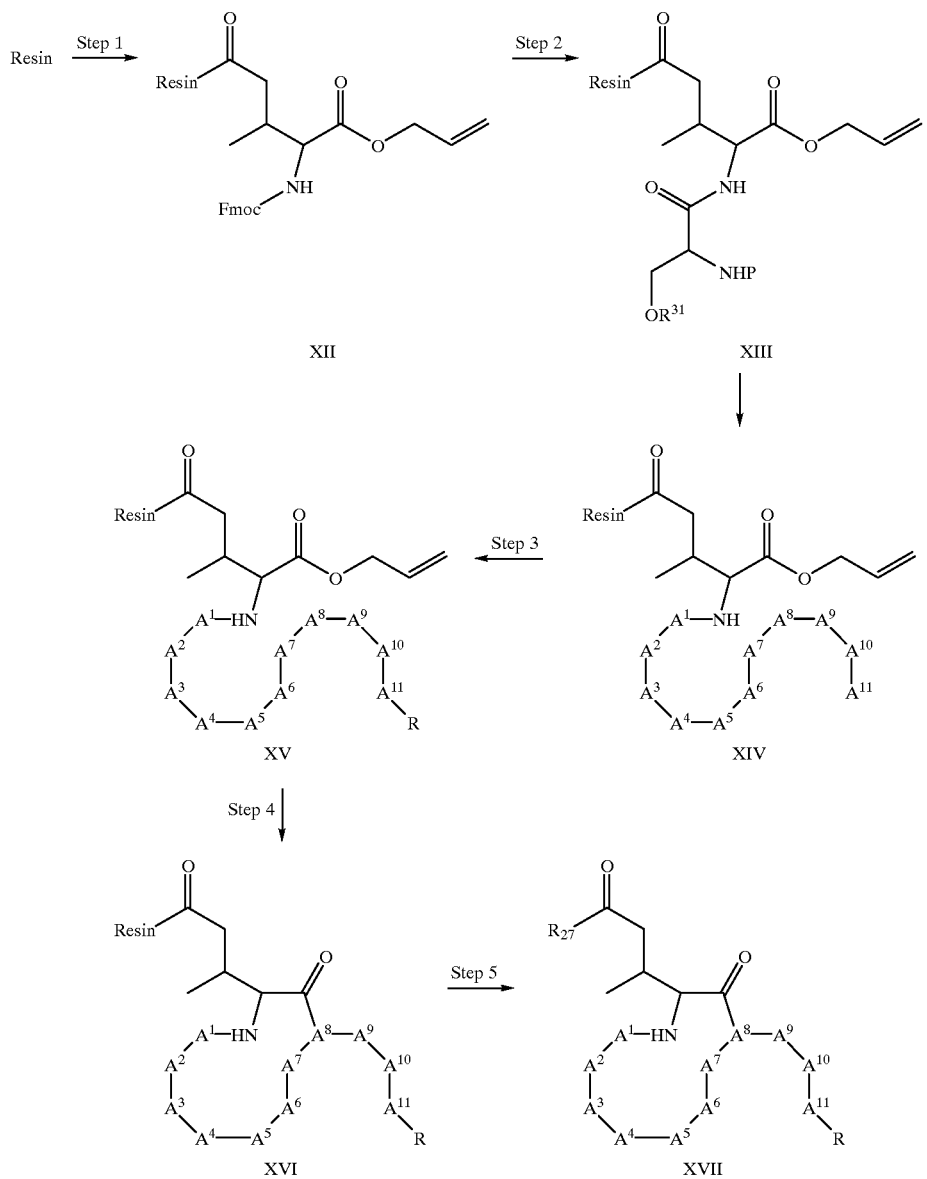
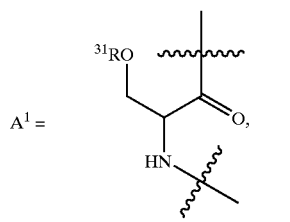
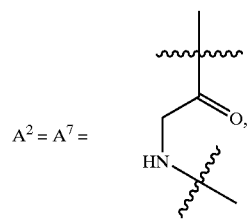
wherein $A^1$, is a suitably protected serine derivative, wherein $R^{31}$ is a suitable, cleavable hydroxyl protecting group as outlined below.
wherein $A^2$ and $A^7$, are suitably protected glycine derivatives as outlined below.

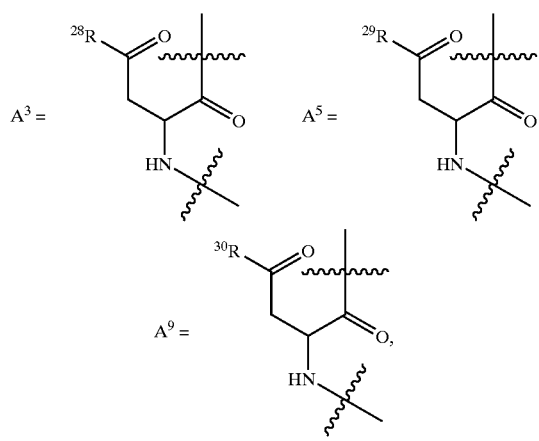

wherein $A^3$, $A^5$ and $A^9$ are suitably protected aspartic acid derivatives as outlined below, wherein $^{28}R$, $^{29}R$ and $^{30}R$ are cleavable protecting groups, preferably t-butyl groups.

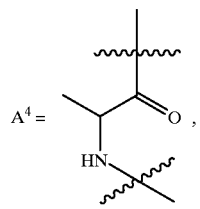

wherein $A^4$ is a suitably protected alanine derivative as outlined below.

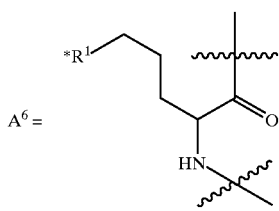

wherein $A^6$ is a suitably protected ornithine derivative as outlined below, or derivatized ornthine wherein $*R^1$ is $R^1$ as previously described or alternatively a protected form of R that would yield $R^1$ upon subsequent deprotection.

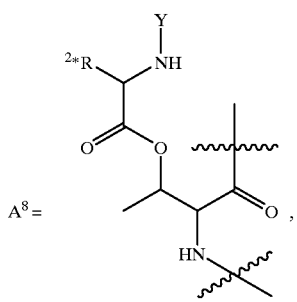

wherein $A^8$ is a suitably protected depsipeptide as outlined below, Y is a protecting group that is cleavable under conditions that leave other protecting groups intact, i.e., Alloc; and wherein $*R^2$ is $R^2$ as previously described or alternatively a protected form of $R^2$ that would yield $R^2$ upon subsequent deprotection. Preferably $*R^2$ is a kynurenine, or substituted kynurenine side chain, most preferably

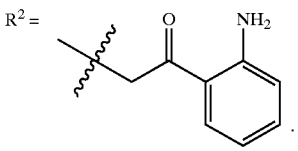

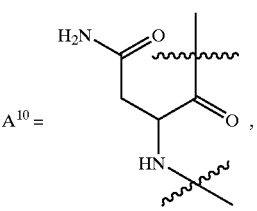

wherein $A^{10}$ is a suitably protected asparagine derivative as outlined below.

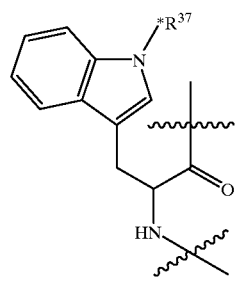

wherein $A^{11}$ is a suitably protected tryptophan derivative as outlined below, wherein $R^{*37}$ is hydrido or a suitable protecting group, preferably t-butoxy carbonyl.

It will be understood by those skilled in the art that both the amino and the side chain functional groups must be suitably protected prior to attaching them to the growing peptide chain. Suitable protecting groups can be any group known in the art to be useful in peptide synthesis. Such pairings of protecting groups are well known. See, e.g., "Synthesis Notes" in the Novabiochem Catalog and Peptide Synthesis Handbook (1999), pages S1–S93 and references cited therein. Following the disclosure of the present application, the selection of protecting groups and method of use thereof will be known to one skilled in the art.

It will also be understood by those skilled in the art that the choice of protecting group on the side chain functional groups will either result or not result in the protecting group being cleaved concomitantly with the peptide's final cleavage from the resin, which will give the natural amino acid functionality or a protected derivative thereof, respectively.

The following general procedures serve to exemplify the solid support synthesis of compounds of Formula I.

Step 1: Coupling Suitably N-protected-βMeGlu(OH)—OAllyl Ester to a Resin

Five molar equivalents each, with respect to the resin, of a suitably-N-protected-βMeGlu(OH)—OAllyl ester, 1,3-Diisopropylcarbodiimide (DIC) and 1-Hydroxy-7-azabenzotriazole (HOAt) are stirred for 30 mins in dimethylformamide (DMF; 5 ml/g resin). A suitably functionalised resin or solid support, such as, but not limited to, Wang, Safety Catch, Rink, Knorr, PAL, or PAM resin, is added and the resulting suspension is stirred for 16 hrs. The resin-N-protected-βMeGlu(OH)—OAllyl ester is then filtered, dried and the coupling is repeated. The N-protecting group is then removed using the appropriate conditions given in the coupling steps below.

Step 2: (A) General Coupling Cycle for Amino Acids with an N-9-Fluorenylmethoxycarbonyl (Fmoc) Protecting Group Five molar equivalents each, with respect to the resin-AA(wherein resin-AA is defined as the resin attached the the growing amino acid chain), of a suitably protected Fmoc amino acid, DIC, and HOAt (0.5 molar solution in DMF) are added to the resin-AA, along with sufficient DMF to give a working volume. The mixture is shaken for one hour, filtered, and the coupling is repeated. After the second coupling the resin is washed twice with DMF, twice with methanol, and twice again with DMF. The Fmoc group of the newly coupled amino acid $A^{1-11}$ is deprotected by stirring the resin product in one working volume of a solution of 20% piperidine in N-methyl pyrolidine for five minutes, filtering the resin, and stirring the resin in 20% piperidine in N-methyl pyrolidine again for 20 minutes. The resin is washed twice with DMF, twice with methanol, and twice again with DMF.

Step 2 (B): General Coupling Cycle of Amino Acids with an N-tert-Butoxy-carbonyl (N-Boc) Protecting Group Five molar equivalents each, with respect to the resin-AA, of a suitably protected N-Boc amino acid, DIC, and HOAt (0.5 molar solution in DMF) are added to the resin-AA, along with sufficient DMF to give a working volume. The mixture is shaken for one hour, filtered, and the coupling is repeated. After the repeated coupling the resin is washed twice with DMF, twice with methanol, and twice again with DMF. The Boc group of the newly coupled amino acid $A^{1-11}$, is then deprotected by stirring the resin in one working volume of $CH_2Cl_2$:trifluoroacetic acid (TFA) 1:1 for 15 minutes, filtering, and stirring in one working volume of $CH_2Cl_2$:TFA 1:1 for another 15 minutes. The resin is neutralized by washing with excess diisopropylethylamine (DIPEA) in $CH_2Cl_2$ and then washed twice with DMF, twice with methanol, and twice again with DMF.

Step 3: Terminal Amine Capping Reaction

Ten molar equivalents, with respect to the resin XV, of a suitable reagent containing R* such as an activated ester, isocyanate, thioisocyanate, anhydride, acid chloride, chloroformate, or reactive salt thereof, in one working volume of DMF is added to the resin XIV and agitated for 25 hours. The resulting resin XV is washed twice with DMF, twice with methanol, and twice again with DMF.

Step 4: Cyclization

The dried resin XV is placed under an argon atmosphere, and treated with a solution of $Pd(PPh_3)_4$ 125 mgs/0.1 mmol peptide substrate, in $CH_2Cl_2$: Acetic acid: N-Methylmorpholine, 40:2:1, 1 ml/0.1 mmol peptide substrate. The mixture is stirred for 3 hours at ambient temperature, filtered, and washed twice with DMF, twice with methanol, and twice again with DMF. Five molar equivalents each, with respect to the resin, of DIC, and HOAt (0.5 molar solution in DMF) are added to the resin, along with sufficient DMF to give a working volume. The reaction is shaken for 17 hours, filtered, and washed twice with DMF, twice with methanol, and twice again with DMF to give resin XVI.

Step 5: Cleavage and Isolation of the Lipopeptide

The desired lipopeptide is cleaved from resin XVI and isolated, resulting in a compound in which $R^{27}$ is OH or $NH_2$. If Fmoc chemistry is used, the dried resin is suspended in 1 ml/0.1 mmol peptide substrate of $CH_2Cl_2$:TFA:Ethanedithiol (EDT):Triisopropylsilane (TIS), 16:22:1:1, and stirred for 6–8 hours at ambient temperature. The resin is filtered, washed with 1 equal volume of cold TFA, and the combined filtrates are evaporated under reduced pressure. Crude product XVII is then precipitated by the addition of diethyl ether, and isolated by centrifugation. This product may be further purified by preparative reverse phase HPLC.

If N-Boc chemistry is used, the dried resin is suspended in hydrogen flouride (HF):anisole:dimethylsulfide (DMS), 10:1:1 and stirred for 2 hours at 0° C. The volitiles are evaporated under a stream of nitrogen. The resin is then extracted with TFA, filtered and washed twice with TFA, and the combined TFA filtrates evaporated under reduced pressure. Crude product is then precipitated by the addition of diethyl ether, and isolated by centrifugation. This product may be further purified by preparative reverse phase HPLC.

If the resin is a Safety Catch resin, then R=OR or NRH. The dried resin XVI is suspended in N-methylpyrolidine (NN) or dimethylsulphoxide (DMSO) (8 ml/g resin), Five equivalents of DIPEA (with respect to resin substitution) and 24 equivalents of iodo or bromoacetonitrile (with respect to resin substitution) are added. The suspension is stirred for 24 hours at ambient temperature under inert atmosphere. The resin is filtered, washed with tetrahydrofuran (THF) and DMSO. For an ester, the resin is then treated with an alcohol, hydroxide or alkoxide (20 equivalents with respect to resin substitution) in THF for 20 hours. The resin is filtered, washed with THF and water, and the combined filtrates are evaporated under reduced pressure. Crude product is precipitated by the addition of diethyl ether, and isolated by centrifugation. The product may be further purified by preparative reverse phase HPLC. For amides the resin is then treated with a primary or secondary amine (20 equivalents with respect to resin substitution) in TMF for 12–40 hours, at a gentle reflux under inert atmosphere. The resin is filtered, washed with THF and water, and the combined filtrates are evaporated under reduced pressure. Crude product is then precipitated by the addition of diethyl ether, and isolated by centrifugation. This product may be further purified by preparative reverse phase HPLC.

In order that this invention may be more fully understood, the following examples are set forth. These examples are for the purpose of illustration only and are not to be construed as limiting the scope of the invention in any way.

EXAMPLE 1

Preparation of Compounds 2, 3 and 4

Sulfamic acid (89.9 mg) and sodium nitrite (51.1 mg) were added to a solution of daptomycin (1 g) in 0.1 M hydrochloric acid (31 ml) at 0° C. After 15 minutes a solution of potassium O-ethylxanthic acid (497 mg) in water (5 ml) was added and the mixture was heated to 60° C. for 1 hour. After cooling to room temperature the mixture was adjusted to pH 6–7 with solid sodium bicarbonate and purified by preparative HPLC column chromatography. An IBSIL-C8 5µ 250×20.2 mm column was loaded with the daptomycin mixture and eluted at 20 ml/min with a gradient of 100–55% Buffer A (38% acetonitrile in 5 mM ammonium phosphate buffer) to 0–45% Buffer B (90% acetonitrile in water). Fractions containing the desired compound were collected and freeze-dried. The freeze-dried residue was dissolved in water (5 ml) and applied to a Bondesil 40µ C8 resin column, washed with water and eluted with methanol. Evaporation of the methanol gave Compound 3 as a pale yellow solid (103.8 mg).

In an analogous manner, compounds 2 and 4 were prepared as detailed in the above example by substituting an appropriate xanthate salt in place of potassium O-ethylxanthic acid.

EXAMPLE 2

Preparation of Compounds 1, 7, 10–12 and 13

Daptomycin (162 mg) was stirred in 0.1 M hydrochloric acid (5 ml) at 0° C. for 10 minutes before sodium nitrite (8 mg) in water (0.2 ml) was added dropwise. Sulfamic acid (11 mg) was added after 15 minutes, followed by sodium azide (8 mg) 10 minutes later. The mixture was maintained at 0° C. for 4 hours and then was neutralized with saturated sodium bicarbonate solution and purified by preparative HPLC. The mixture was loaded on an IBSIL-C8 $5\mu$ 250×20.2 mm column and was eluted at 20 m/min with 37% acetonitrile in 5 mM ammonium phosphate buffer. The desired fractions were collected at 6.9 minutes and freeze dried. The freeze dried residue was dissolved in water (5 ml) and applied to a Bondesil $40\mu$ C8 resin column. The column was washed with water and eluted with methanol. Evaporation of the methanol gave Compound 1 as a pale yellow solid (60 mg).

Compound 1 (30 mg) and hydroxylamine hydrochloride (100 mg) in water (2 ml) were stirred at room temperature for 24 hours. The mixture was purified by preparative HPLC by loading onto an IBSIL-C8 $5\mu$ 250×20.2 mm column and eluting the column at 20 ml/min with 32% acetonitrile in 5 mM ammonium phosphate buffer. The desired fractions were collected at 15 minutes and freeze dried. The freeze dried residue was dissolved in water (5 ml) and applied to a Bondesil $40\mu$ C8 resin column. The column was washed with water and eluted with methanol. Evaporation of the methanol gave Compound 7 as a pale yellow solid (5 mg).

Compound 1 (69 mg) was dissolved in dimethylformamide (4 ml) and iminobiotin-N-hydroxysucciniminde ester (53 mg) was added. The mixture was covered to exclude light and was stirred at ambient temperature for 3 days. The mixture was quenched by the addition of water (20 ml). The resultant mixture was loaded onto a Bondesil $40\mu$ C8 resin (25 g) column, which had been previously washed with methanol and water. The column was eluted with water. The product-bearing fractions were combined and freeze dried to give Compound 11 as a white solid (49 mg).

In an analogous manner, Compounds 10 and 12 can be prepared as detailed in the above example by substituting N-methyl isatoic anhydride or N-Boc tyrosine pentafluorophenol ester respectively in place of iminobiotin-N-hydroxysuccinimide ester. Compound 12 requiring additional deprotection of the Boc group according to standard procedures known to those skilled in the art. Compound 13 can be prepared as detailed in the above example by substituting O-methylhydroxylamine hydrochloride for hydroxylamine hydrochloride.

EXAMPLE 2a

Preparation of Compound 15

To compound 1(100 mg) in ethylene glycol (5 ml) was added camphorsulfonic acid (28 mg). The mixture was stirred at 0° C. for 24 hours before being purified by preparative HPLC. The mixture was loaded on an IBSIL-C8 $5\mu$ 250×20.2 mm column and eluted at 20 ml/min with 36% acetonitrile in 5 mM ammonium phosphate buffer. The desired fractions were collected at 25 minutes and freeze-dried. The freeze-dried residue was dissolved in water (2 ml) and applied to a plug of Bondesil $40\mu$ C8 resin (500 mg). The Bondesil resin was washed with water (10 ml) and the product was eluted off with methanol (10 ml). Evaporation of the methanol gave compound 15 as a pale yellow solid (3 mg).

EXAMPLE 2b

Preparation of Compound 16

To compound 1 (100 mg) in methanol (5 ml) was added sodium borohydride (46 mg). The mixture was stirred at room temperature for 24 hours before being purified by preparative HPLC. The reaction was loaded on an IBSIL-C8 $5\mu$ 250×20.2 mm column and eluted at 20 ml/min with 33% acetonitrile in 5 mM ammonium phosphate buffer. The desired fractions were collected at 19 minutes and freeze-dried. The freeze-dried residue was dissolved in water (2 ml) and applied to a plug of Bondesil $40\mu$ C8 resin (500 mg). The Bondesil resin was washed with water (10 ml) and the product was eluted off with methanol (10 ml). Evaporation of the methanol gave compound 16 as a pale yellow solid (4 mg).

EXAMPLE 3

Preparation of Compounds 5, 6 and 8

Daptomycin (1.62 g) in 50% wt aqueous solution of hypophosphorus acid (10 ml) was stirred at 0° C. for 30 minutes before adding dropwise a solution of sodium nitrite (76 mg) in water (0.5 ml). The mixture was allowed to come to room temperature and was stirred for 24 hours. The mixture was purified by preparative HPLC by loading the mixture on an IBSIL-C8 $5\mu$ 250×20.2 mm column and eluting the column at 20 ml/min with 32% acetonitrile in 5 mM ammonium phosphate buffer. The desired fractions were collected at 30 minutes and freeze dried. The freeze-dried residue was dissolved in water (5 ml) and applied to a Bondesil $40\mu$ C8 resin column. The column was washed with water and eluted with methanol. Evaporation of the methanol gave Compound 5 as a pale yellow solid (200 mg).

Compound 5 (10 mg) and hydroxylamine hydrochloride (100 mg) in water (1 ml) were stirred at room temperature for 24 hours. The mixture was purified by preparative HPLC by loading the mixture on an IBSIL-C8 $5\mu$ 250×20.2 mm column and eluting the column at 20 ml/min with 34% acetonitrile in 5 mM ammonium phosphate buffer. The desired fractions were collected at 12 minutes and freeze dried. The freeze-dried residue was dissolved in water (5 ml) and applied to a Bondesil $40\mu$ C8 resin column. The column was washed with water and eluted with methanol. Evaporation of the methanol gave Compound 6 as a pale yellow solid (4 mg)

In an analogous manner, Compound 8 was prepared as detailed in the above example by substituting O-methylhydroxylamine hydrochloride in place of hydroxylamine hydrochloride.

EXAMPLE 3a

Preparation of Compound 14

To compound 5 (80 mg) in dry dimethylformamide (2 ml) was added N-t-butoxycarbonyl-L-tryptophan-p-nitrophenyl ester (32 mg). The mixture was stirred at room temperature for 24 hours before being purified by preparative HPLC. The mixture was loaded on an IBSIL-C8 $5\mu$ 250×20.2 mm column and eluted at 20 ml/min with 40% acetonitrile in 5 mM ammonium phosphate buffer. The desired fractions were collected at 19 minutes and freeze-dried. The freeze-dried residue was dissolved in water (2 ml) and applied to a plug of Bondesil 40μ C8 resin (500 mg). The Bondesil resin was washed with water (10 ml) and then the product was eluted with methanol (10 ml). Evaporation of the methanol gave Boc protected compound 14 as a pale yellow solid (20 mg).

To Boc protected compound 14 (20 mg) in 60% trifluoroacetic acid in dichloromethane (0.5 ml) was added anisole (10 μL). The mixture was stirred at room temperature for 6 hours before being evaporated to dryness. Preparative HPLC purification of the residue was done on an IBSIL-C8 5μ 250×20.2 mm column and eluted at 20 ml/min with 38% acetonitrile in 5 mM ammonium phosphate buffer. The desired fractions were collected at 15 minutes and freeze-dried. The freeze-dried residue was dissolved in water (2 ml) and applied to a plug of Bondesil 40μ C8 resin (500 mg). The Bondesil resin was washed with water (10 ml) and the product was eluted with methanol (10 ml). Evaporation of the methanol gave compound 14 as a pale yellow solid (4 mg).

EXAMPLE 4

Preparation of Compound 9

Daptomycin (162 mg) was stirred in 1 M hydrochloric acid (5 ml) at 0° C. for 10 minutes before sodium nitrite (8 mg) in water (0.2 ml) was added dropwise. Tin (II) chloride dihydrate (50 mg) was added after 30 minutes, the mixture was allowed to warm to room temperature and then was stirred for 24 hours. The mixture was purified by preparative HPLC by loading the mixture on an IBSIL-C8 5μ 250×20.2 mm column and eluting the column at 20 ml/min with 34% acetonitrile in 5 mM ammonium phosphate buffer. The desired fractions were collected at 15 minutes and freeze dried. The freeze dried residue was dissolved in water (5 ml) and applied to a Bondesil 40μ C8 resin column. The column was washed with water and eluted with methanol. Evaporation of the methanol yielded Compound 9 as a pale yellow solid (33 mg).

EXAMPLE 5

Compounds according to Formula I were tested for antimicrobial activity against a panel of organisms according to standard procedures described by the National Committee for Clinical Laboratory Standards (NCCLS document M7-A5, Vol. 20, No. 2, 2000) except that all testing was performed at 37° C. Compounds were dissolved in 100% dimethyl sulfoxide and were diluted to the final reaction concentration (0.1 μg/mL–100 μg/mL) in microbial growth media. In all cases the final concentration of dimethyl sulfoxide incubated with cells is less than or equal to 1%. For minimum inhibitory concentration (MIC) calculations, 2-fold dilutions of compounds were added to wells of a microtiter plate containing $5\times10^4$ bacteria cells in a final volume of 100 μL of media (Mueller-Hinton Broth supplemented with 50 mg/L $Ca^{2+}$). The optical densities (OD) of the bacterial cells, which measures bacterial cell growth and proliferation, were measured using a commercial plate reader. The MIC value is defined as the lowest compound concentration inhibiting growth of the test organism. The MIC (in 1 g/ml) values of representative compounds of the present invention are listed in Table II.

EXAMPLE 6

The mouse protection test is an industry standard for measuring the efficacy of a test compound in vivo [for examples of this model see J. J. Clement, et al., *Antimicrobial Agents and Chemotherapy*, 38 (5), 1071–1078, (1994)]. As exemplified below, this test is used to demonstrate the in vivo efficacy of the compounds of the present invention against bacteria.

The in vivo antibacterial activity of Compound 5 (see Table II) was established by infecting female CD-1 mice (Charles River Lab, Mass.) weighing 19–23 g intraperitoneally with Methicillin Resistant *S. aureus* (MRSA) inoculum. The inoculum was prepared from Methicillin Resistant *S. aureus* (ATCC 43300). The MRSA inoculum was cultured in Mueller-Hinton (MH) broth at 37° C. for 18 hours. The optical density at 600 nm ($OD_{600}$) was determined for a 1:10 dilution of the overnight culture. Bacteria ($8\times10^8$ cfu) was added to 20 ml of phosphate buffered saline (Sigma P-0261) containing 6% hog gastric mucin (Sigma M-2378). All animals were injected with 0.5 ml of the inoculum, equivalent to $2\times10^7$ cfu/mouse, which is the dose causing 100% death of the animals without treatment.

The test compound was dissolved in 10.0 ml of 50 mM phosphate buffer to give a solution of 1 mg/ml (pH=7.0). This solution was serially diluted with vehicle by 2-fold (4 ml to 8 ml) to give 0.05, 0.025 and 0.0125 mg/ml solutions. All the solutions were filtered with 0.2 μm Nalgene syringe filter. Immediately after the bacterial inoculation, group 1 animals were subcutaneously (sc) injected with buffer (no test compound) and groups 2 to 5 were given test compound sc at 1.0, 0.5, 0.25, and 0.125 mg/kg, respectively. Group 6 animals received only 6% hog mucin at 0.5 ml/mouse i.p. These injections were repeated once at 4 hours after the inoculation for the respective groups. The injection volume at each time was 10 ml per kilogram of body weight. The results of the in vivo efficacy test are summarized in Table II, which provides a representative example of the results obtained for Compound 5. The 50% effective dose ($ED_{50}$) is calculated on the basis of the number of mice surviving 7 days after inoculation.

The $ED_{50}$ was determined for representative compounds of this invention in a similar manner and are listed in Table III.

TABLE II

| Group | # of mice | Inoculated with | Treatment | Survival (7 days) |
|---|---|---|---|---|
| 1 | 5 | MRSA #43300 $2\times10^7$ cfu/mouse | Phosphate buffer 10 ml/kg, s.c. × 2 | 0/5 |
| 2 | 5 | MRSA #43300 $2\times10^7$ cfu/mouse | Compound 5 1 mg/kg, s c. × 2 | 5/5 |
| 3 | 5 | MRSA #43300 $2\times10^7$ cfu/mouse | Compound 5 0.5 mg/kg, s.c. × 2 | 4/5 |
| 4 | 5 | MRSA #43300 $2\times10^7$ cfu/mouse | Compound 5 0.25 mg/kg, s.c. × 2 | 0/5 |
| 5 | 5 | MRSA #43300 $2\times10^7$ cfu/mouse | Compound 5 0.125 mg/kg, s.c. × 2 | 0/5 |
| 6 | 5 | 6% hog mucin 0.5 ml/mouse | NO | 5/5 |

The $ED_{50}$ of compound 5 is calculated to be 0.46 mg/kg

TABLE III

| Compound # | MIC (μg/ml) S. aureus | MIC (μg/ml) E. faecalis | $ED_{50}$ mg/kg |
|---|---|---|---|
| 1 | ++ | ++ | |
| 2 | ++ | + | |

TABLE III-continued

| Compound # | MIC (µg/ml) S. aureus | MIC (µg/ml) E. faecalis | ED$_{50}$ mg/kg |
|---|---|---|---|
| 3 | ++ | ++ | ++ |
| 4 | ++ | + | |
| 5 | ++ | + | +++ |
| 6 | ++ | + | |
| 7 | + | + | |
| 8 | ++ | + | |
| 9 | ++ | + | |
| 10 | ++ | + | |
| 11 | ++ | + | |
| 12 | ++ | + | |
| 13 | + | + | |
| 14 | + | | |
| 15 | + | + | |
| 16 | + | + | |

Wherein "+++" indicates that the compound has an MIC (µg/ml) of 1 µg/ml or less or an ED$_{50}$ of 1 mg/kg or less;
"++" indicates that the compound has an MIC (µg/ml) or an ED$_{50}$ (mg/kg) of more than 1 µg/ml or 1 mg/kg, respectively, but less than or equal to 10 µg/ml or 10 mg/kg, respectively; and
"+" indicates that the compound has an MIC (µg/ml) of greater than 10 µg/ml or an ED$_{50}$ of greater than 10 mg/kg.

All publications and patent applications cited in this specification are herein incorporated by reference as if each individual publication or patent application were specifically and individually indicated to be incorporated by reference. Although the foregoing invention has been described in some detail by way of illustration and example for purpose of clarity of understanding, it will be readily apparent to those of ordinary skill in the art in light of the teachings of this invention that certain changes and modifications may be made thereto without departing from the spirit or scope of the appended claims.

We claim:

1. A compound having the formula (I):

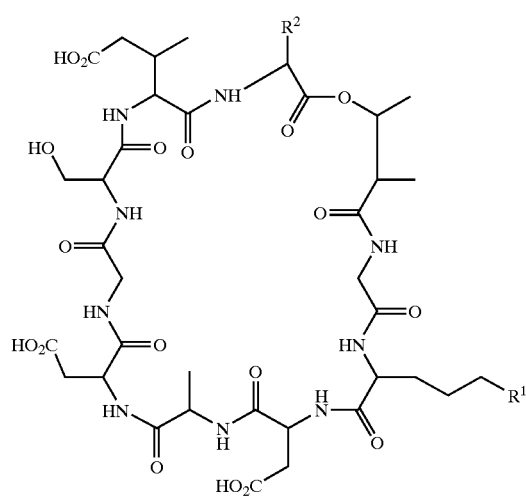

(I)

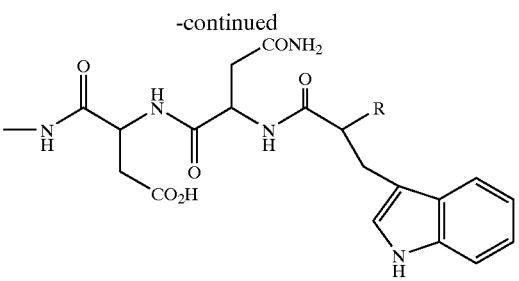

or a salt thereof;

wherein R and $R^1$ are independently:

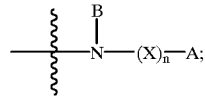

wherein X and X' are independently selected from the group consisting of C=O, C=S, C=NH, C=$NR^X$, S=O and $SO_2$;

wherein n is 0 or 1;

wherein $R^X$ is selected from the group consisting of alkyl, alkenyl, alkynyl, aryl, heteroaryl, cycloalkyl, heterocyclyl, hydroxyl, alkoxy, carboxy and carboalkoxy;

wherein B is X'$R^Y$, H, alkyl, alkenyl, alkynyl, aryl, heteroaryl, cycloalkyl or heterocyclyl;

wherein $R^Y$ is selected from the group consisting of hydrido, alkyl, alkenyl, alkynyl, aryl, heteroaryl, cycloalkyl, heterocyclyl and hydroxyl;

wherein A is H, $NH_2$, $NHR^A$, $NR^AR^B$, alkyl, alkenyl, alkynyl, alkoxy, aryloxy, aryl, heteroaryl, cycloalkyl, or heterocyclyl;

wherein $R^A$ and $R^B$ are independently selected from the group consisting of alkyl, alkenyl, alkynyl, aryl, heteroaryl, cycloalkyl, heterocyclyl and carboalkoxy; or wherein when n is 0, then A is additionally selected from the group consisting of:

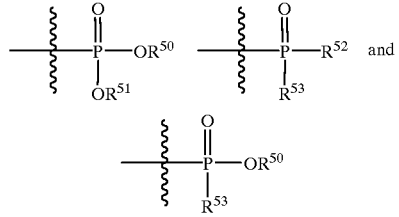

wherein each of $R^{50}$–$R^{53}$ is independently selected from $C_1$–$C_{15}$ alkyl;

alternatively, wherein B and A together form a 5–7 membered heterocyclic or heteroaryl ring; and wherein R² is

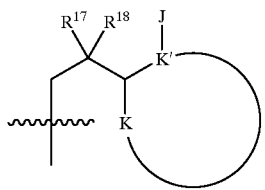

wherein K and K' together form a C₃–C₇ cycloalkyl or heterocyclyl ring or a C₅–C₁₀ aryl or heteroaryl ring;

wherein J is selected from the group consisting of hydrido, amino, NHR$^J$, NR$^J$R$^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

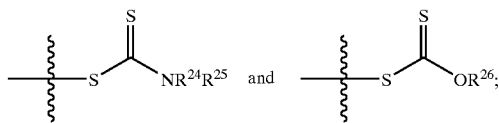

wherein each of R²⁴, R²⁵, and R²⁶ is independently selected from the group consisting of alkyl, cycloalkyl, heterocyclyl, aryl and heteroaryl; or R²⁴ and R²⁵ together form a 5–8 membered heterocyclyl ring;

wherein R$^J$ and R$^K$ are independently selected from alkyl, alkenyl, alkynyl, aryl, heteroaryl, cycloalkyl or heterocyclyl; or alternatively, wherein J, together with R¹⁷, forms a 5–8 membered heterocyclyl or cycloalkyl, ring; or alternatively, J, together with both R¹⁷ and R¹⁸, forms a 5–8 membered aryl, cycloalkyl, heterocyclyl or heteroaryl ring;

wherein each of R¹⁷ and R¹⁸ is independently selected from the group consisting of hydrido, halo, hydroxyl, alkoxy, amino, thio, sulfinyl, sulfonyl and

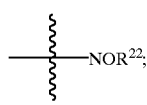

or wherein R¹⁷ and R¹⁸ taken together form a substituent selected from the group consisting of ketal, thioketal,

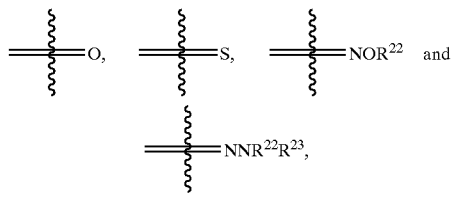

wherein each of R²² and R²³ is independently selected from the group consisting of hydrido and alkyl;

provided that when K and K' are together form a phenyl ring and R¹⁷ and R¹⁸ taken together form C=O, then J is not NH₂, C₄–C₁₄ alkylidenyl, or NHR$^Q$, wherein R$^Q$ is C₄–C₁₄ unsubstituted alkyl, substituted or unsubstituted C₂–C₁₉ alkanoyl, unsubstituted C₅–C₁₉ alkenoyl, benzyloxycarbonyl, or carboalkoxy.

2. The compound according to claim 1, wherein R is selected from the group consisting of:

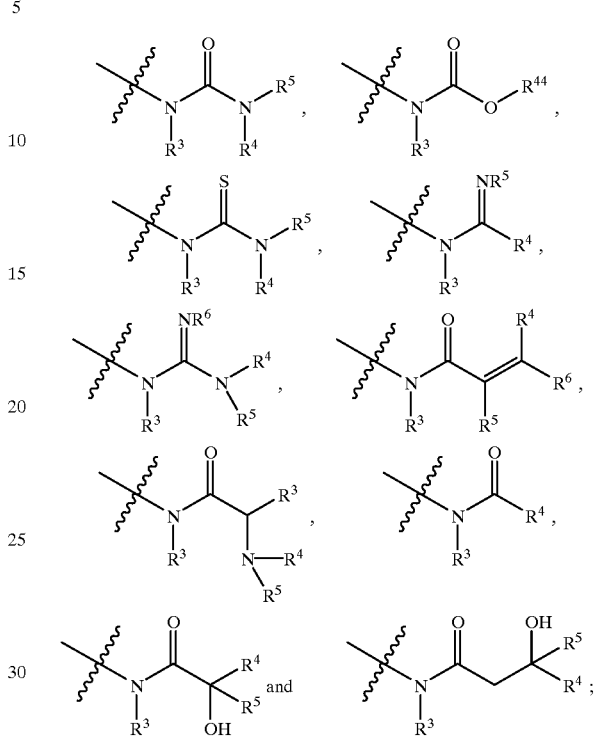

wherein each of R³, R⁴ R⁵, and R⁶ is independently selected from the group consisting of hydrido, alkyl, aryl, heterocyclyl and heteroaryl, and wherein R⁴⁴ is selected from the group consisting of alkyl, aryl, heterocyclyl and heteroaryl.

3. The compound according to claim 2, wherein R is selected from the group consisting of

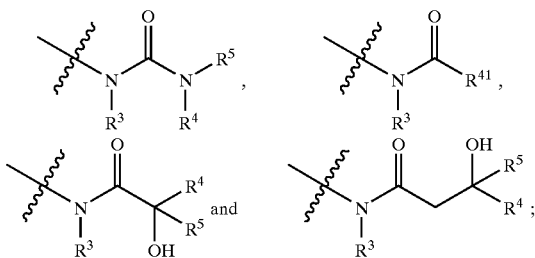

wherein R⁴' is selected from the group consisting of alkcyl, aryl-substituted alkyl, substituted phenyl, heteroaryl, heterocyclyl, optionally substituted (C₈–C₁₄)-straight chain alkyl and

wherein R⁷ is an alkyl group.

4. The compound according to claim 3, wherein R is selected from the group consisting of

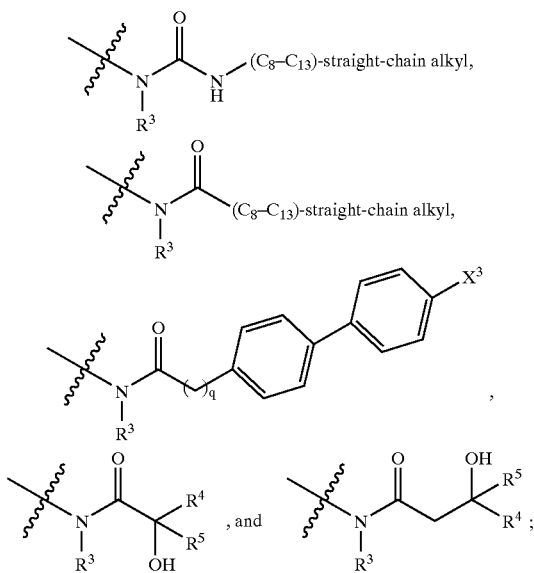

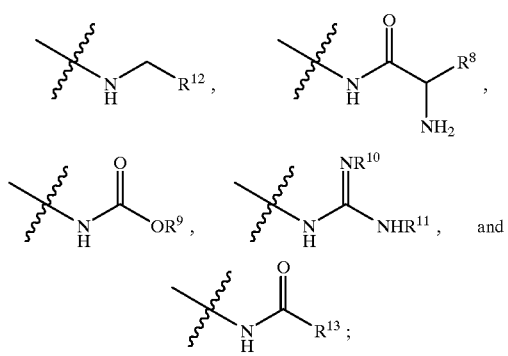

wherein X³ is chloro or trifluoromethyl and wherein q is 0 or 1.

5. The compound according to claim 1, wherein R¹ is selected from the group consisting of:

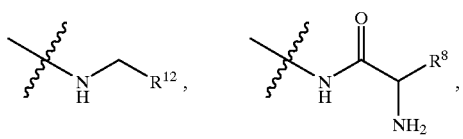

wherein R⁸ is selected from an amino acid side chain, wherein said amino acid side chain may be one that is naturally occurring or one that is not naturally occurring;

wherein each of R⁹, R¹⁰ and R¹¹ is selected from the group consisting of hydrido, alkyl, aryl, heterocyclyl and heteroaxyl;

wherein R¹² is selected from the group consisting of heterocyclyl, heteroaryl, aryl, and alkyl and wherein R¹³ is selected from the group consisting of (C₁–C₃)-alkyl and aryl.

6. The compound according to claim 5, wherein R¹ is selected from the group consisting of:

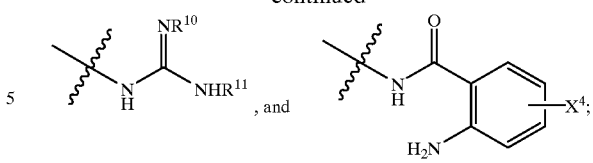

wherein R⁸ is selected from the group consisting of a tryptophan side chain and a lysine side chain;

wherein each of R¹⁰ and R¹¹ is independently selected from the group consisting of hydrido and alkyl;

wherein R¹² is selected from the group consisting of imidazolyl, N-methylimidazolyl, indolyl, quinolinyl, benzyloxybenzyl, and benzylpiperidenylbenzyl; and wherein X⁴ is selected from the group consisting of fluoro and trifluoromethyl.

7. The compound according to claim 1, wherein J is selected from the group consisting of hydrido, amino, azido and

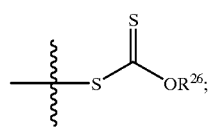

wherein R¹⁷ and R¹⁸ taken together form a substituent selected from the group consisting of ketal,

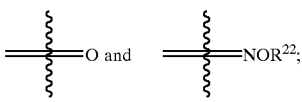

or wherein R¹⁷ is hydroxyl when R¹⁸ is hydrido;

or wherein J, together with R¹⁷, forms a heterocyclyl ring.

8. The compound of claim 7, wherein R² is selected from the group consisting of

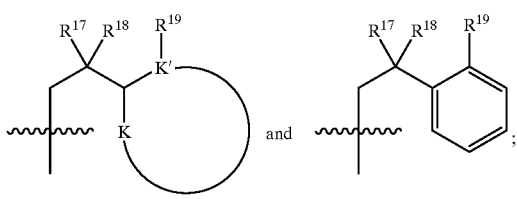

wherein R¹⁷ and R¹⁸ taken together form a substituent selected from the group consisting of

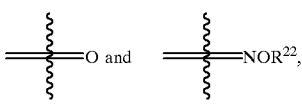

wherein R²² is selected from the group consisting of H and alkyl; and wherein R¹⁹ is selected from the group consisting of hydrido, amino, azido and

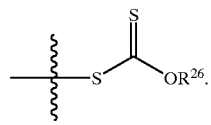

5

9. The compound according to claim 1, wherein said compound is selected from:

| Cpd # | R | R¹ | R² |
|---|---|---|---|
| 1 | NHCO(CH$_2$)$_8$CH$_3$ | NH$_2$ | 2-azidophenyl ketone |
| 2 | NHCO(CH$_2$)$_8$CH$_3$ | NH$_2$ | 2-(diethylthiocarbamoylthio)phenyl ketone |
| 3 | NHCO(CH$_2$)$_8$CH$_3$ | NH$_2$ | 2-(ethoxythiocarbonylthio)phenyl ketone |
| 4 | NHCO(CH$_2$)$_8$CH$_3$ | NH$_2$ | 2-(pyrrolidinylthiocarbonylthio)phenyl ketone |
| 5 | NHCO(CH$_2$)$_8$CH$_3$ | NH$_2$ | phenyl ketone |
| 6 | NHCO(CH$_2$)$_8$CH$_3$ | NH$_2$ | phenyl oxime |
| 7 | NHCO(CH$_2$)$_8$CH$_3$ | NH$_2$ | 2-azidophenyl oxime |

-continued
| Cpd # | R | R¹ | R² |
|---|---|---|---|
| 8 | NHCO(CH$_2$)$_8$CH$_3$ | NH$_2$ | 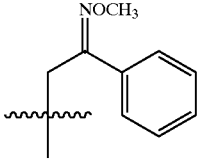 |
| 9 | NHCO(CH$_2$)$_8$CH$_3$ | NH$_2$ | 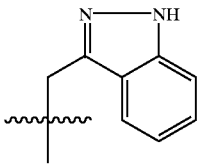 |
| 10 | NHCO(CH$_2$)$_8$CH$_3$ | 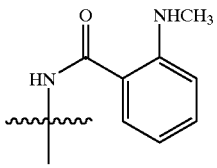 | 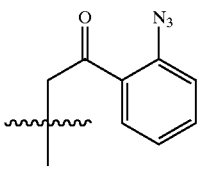 |
| 11 | NHCO(CH$_2$)$_8$CH$_3$ | 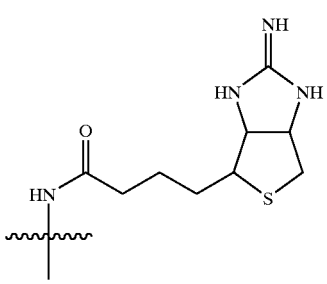 | 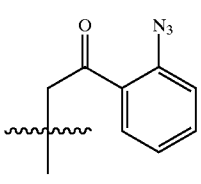 |
| 12 | NHCO(CH$_2$)$_8$CH$_3$ | 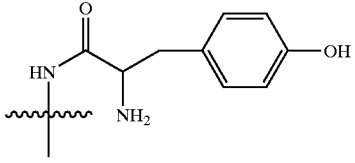 | 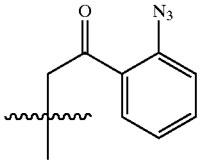 |
| 13 | NHCO(CH$_2$)$_8$CH$_3$ | NH$_2$ | 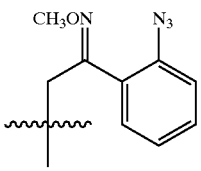 |
| 14 | NHCO(CH$_2$)$_8$CH$_3$ | 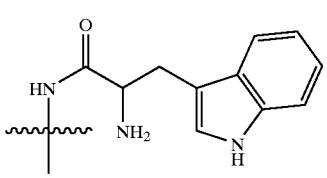 | 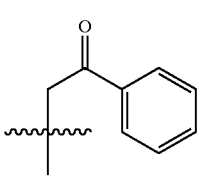 |
| 15 | NHCO(CH$_2$)$_8$CH$_3$ | NH$_2$ | 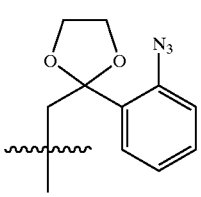 |

-continued
| Cpd # | R | R¹ | R² |
|---|---|---|---|
| 16 | NHCO(CH$_2$)$_8$CH$_3$ | NH$_2$ | 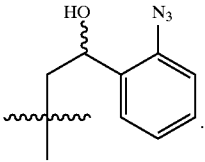 |
10. The compound according to claim 1, wherein R is selected from
NHCO[(C$_6$–C$_{14}$)-alkyl]-CH$_3$, and R¹ and R² are selected from
| R¹ | R² |
|---|---|
| NH$_2$ | 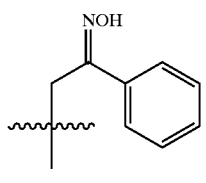 |
| NH$_2$ | 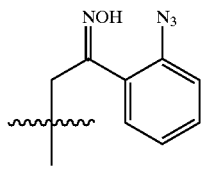 |
| NH$_2$ | 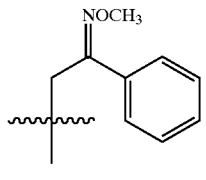 |
| NH$_2$ | 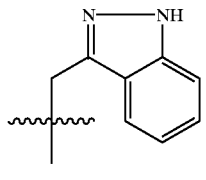 |
| NH$_2$ | 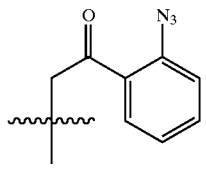 |
-continued
| R¹ | R² |
|---|---|
| NH$_2$ | |
| NH$_2$ | |
| NH$_2$ | |
| NH$_2$ | |
| NH$_2$ | |

-continued

| R¹ | R² |
|---|---|

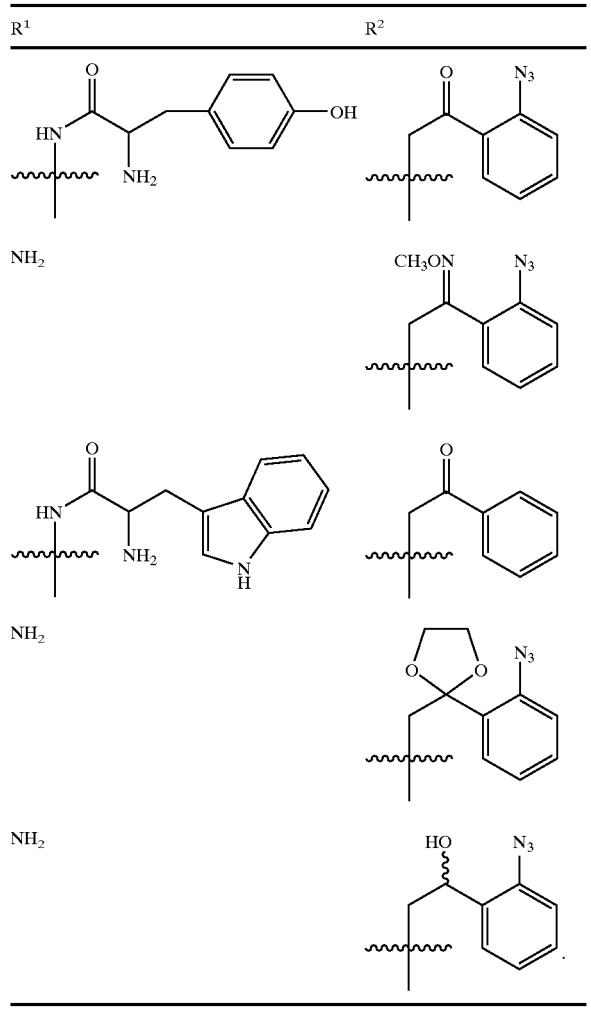

11. A compound according to claim 10, wherein R is selected from NHCO[(CH$_2$)$_{6-14}$]—CH$_3$.

12. A pharmaceutical composition comprising the compound according to claim 1 and a pharmaceutically acceptable carrier.

13. A method of treating a bacterial infection in a subject, comprising the step of administering a compound according to claim 1 or a pharmaceutical composition comprising said compound and a pharmaceutically acceptable carrier to a subject in need thereof for a time and under conditions effective to ameliorate said bacterial infection.

14. The method according to claim 13, wherein said subject is selected from the group consisting of a human, an animal, a cell culture and a plant.

15. The method according to claim 14, wherein said bacterial infection is caused by a gram-positive bacteria.

16. The method according to claim 13, wherein said bacteria is an antibiotic-resistant bacteria.

17. The method according to claim 16, wherein said antibiotic-resistant bacteria are resistant to an antibiotic selected from the group consisting of vancomycin, methicillin, glycopeptide antibiotics, penicillin and daptomycin.

18. The method according to claim 13, further comprising the step of co-administering more than one compound of Formula (I) to a subject in need thereof.

19. The method according to claim 13, further comprising the step of co-administering an antimicrobial agent other than a compound of Formula (I) to a subject in need thereof.

20. The method according to claim 19, wherein said antimicrobial agent is selected from the group consisting of penicillins, carbapenems, cephalosporins, amninoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, trimethoprim, pyrimethamine, synthetic antibacterials, nitroimidazoles, quinolones, fluoroquinolones, isoniazid, ethambutol, pyrazinamide, pera-aminosalicylic acid (PAS), cycloserine, capreomycin, ethionamide, prothionamide, thiacetazone, viomycin, eveminomicins, glycopeptides, glycylcyclines, ketolides, oxazolidinones, imipenen, amikacin, netilmicin, fosfomycin, gentamicin, ceftriaxone, Ziracin (56-deaceytl-57-dimethyl-45-O-de(2-methyl-1-oxopropyl)-12-O-(2,3,6-trideoxy-3-C-methyl-4-O-methyl-3-nitro-alpha-L-arabino-hexopyranosyl)flambamycin), LY333328 (oritavancin), Linezolid (N-[[(5S)-3-[3-fluoro-4-(4-morpholinyl) phenyl]-2-oxo-5-oxazolidinyl]methyl] acetamide), Synercid (dalfopristin-quinupristin), Aztreonam (2-[[(Z)-[1-(2-amino-4-thiazolyl)-2-[[(2S,3S)-2-methyl-4-oxo-1-sulfo-3-azetidinyl]amino]-2-oxocthylidene]amino] oxy]-2-methyl-propanoic acid), Metronidazole (2-methyl-5-nitro-1H-imidazole-1-ethanol), Epiroprim (5-([[3,5-diethoxy-4-(1H-pyrrol-1-yl)phenyl]methyl]-2,4-pyrimidinediamine), OCA-983 (1-[[(2S)-2-amino-3-methyl-1-oxobutyl]amino]-2,5-anhydro-3-S-[(4R,5S,6S)-2-carboxy-6-[(1R)-1-hydroxyethyl]-4-methyl-7-oxo-1-azabicyclo[3.2.0]hept-2-en-3-yl]-1,4-dideoxy-3-thio-D-threo-pentitol), GV-143253 (trinem), Sanfetrinem ((1S,5S,8aS,8bR)-1,2,5,6,7,8,8a,8b-octahydro-1-[(1R)-1-hydroxyethyl]-5-methoxy-2-oxo-azeto[2,1-a]isoindole-4-carboxylic acid), CS-834 ((4R,5S,6S)-6-[(1R)-1-hydroxyethyl]-4-methyl-7-oxo-3-[[(3R)-5-oxo-3-pyrrolidinyl]thio]-1-azabicyclo[3,2,0]hept-2-ene-2-carboxylic acid(2,2-dimethyl-1-oxopropoxy)methyl ester), Biapenem (6-[[(4R,5S,6S)-2-carboxy-6-[(1R)-1-hydroxyethyl]-4-methyl-7-oxo-1-azabicyclo[3.2.0]hept-2-en-3-yl]thio]-6, 7-dihydro-5H-pyrazolo[1,2-a][1,2,4]triazol-4-ium inner salt), KA 159 (stipiamide), Dynemicin A ((1S, 4R,4aR,14S,14aS,18Z)-1,4,7,12,13, 14-hexahydro-6,8,11-trihydroxy-3-methoxy-1-methyl-7,12-dioxo-4a, 14a-epoxy-4, 14-[3]hexene[1,5]diynonaphtho[2,3-c]phenanthridine-2-carboxylic acid), DX8739 ((4R,5S,6S)-3[[(3S,5S)-5[[4-[(2S)-5-amino-2-hydroxy-1-oxopentyl]-1-piperazinyl] carbonyl]-3-pyrrolidinyl]thio]-6-[(1R)-1-hydroxyethyl]-4-methyl-7-oxo-1-azabicyclo[3.2.0]hept-2-ene-2-carboxylic acid), DU 6681((4R,5S,6S)-3-[[(6S)-6,7-dihydro-5H-pyrrol [1,2-a]imidazol-6-yl]thio]-6-[(1R)-1-hydroxyethyl]-4- methyl-7-oxo-1-azabicyclo[3.2.0]hept-2-ene-2-carboxylic acid), Cefluprenam ((2E)-N-(2-amino-2-oxoethyl)-3-[(6R,7R)-7-[[(2Z)-(5-amino-1,2,4-thiadiazol-3-yl)[(fluoromethoxy)imino]acetyl]amino]-2-carboxy-8-oxo-5-thia-1-azabicyclo[4.2.0]oct-2-en-3-yl]-N-ethyl-N-methyl-2-propen-1-aminium inner salt), ER 35786 ((4R,5S,6S)-6-[(1R)-1-hydroxyethyl]-3-[[(3S,5S)-5-[(R)-hydroxy(3R)-3-pyrrolidinylmethyl]-3-pyrrolidinyl]thio]-4-methyl-7-oxo-1-azabicyclo[3.2.0]hept-2-ene-2-carboxylic acid monohydrochloride), Cefoselis ((6R,7R)-7-[[(2Z)-(2-amino-4-thiazolyl)(methoxyimino)acetyl]amino]-3[[2,3-dihydro-2-(2-hydroxyethyl)-3-imino-1H-pyrazol-1-yl]methyl]-8-oxo-5-thia-1-azabicyclo[4.2.0]oct-2-ene-2-carboxylic acid), Sanfetrinem celexetil ((1S,5S,8aS,8bR)-1,2,5,6,7,8,8a,8b-octahydro-1-[(1R)-1-hydroxyethyl]-5-methoxy-2-oxo-azeto[2,1-a]isoindole-4-carboxylic acid 1-[(cyclohexyloxy)carbonyl]oxy]ethyl ester), HGP-31 (Cefpirome; 1-[[((6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-6,7-dihydro-5H-cyclopenta[b]pyridinimium inner salt), HMR-3647 (3-de[(2,6-dideoxy-3-C-methyl-3-O-methyl-alpha-L-ribo-hexopyranosyl)oxy]-11,12-dideoxy-6-O-methyl-3-oxo-12,11-[oxycarbonyl[[4-[4-(3-pyridinlyl)-1H-imidazol-1-yl]butyl]imino]]-erythromycin), RU-59863 (C-7 catechol substituted cephalosporin), KP 736 ((6R,7R)-7[[((2Z)-(2-amino-4-thiazolyl)[[(1,4-dihydro-1,5-dihydroxy-4-oxo-2-pyridinyl)methoxy]imino]acetyl]amino]-8-oxo-3[(1,2,3thiadiazol-5-ylthio)methyl]-5-thia-1-azabicyclo[4.2.0]oct-2-ene-2-carboxylic acid disodium salt), Rifalazil (1',4-didehydro-1-deoxy-1,4-dihydro-3'-hydroxy-5'-[4-(2-methylpropyl)-1-piperazinyl]-1-oxo-rifamycin VIII), MEN 10700 ((5R,6S)-3[[(2-amino-2-oxoethyl)methylamino]methyl]-6-[(1R)-1-hydroxyethyl]-7-oxo-4-thia-1-azabicyclo[3.2.0]hept-2-ene-2-carboxylic acid), Lenapenern ((4R,5S,6S)-6[(1R)-1-hydroxyethyl]-3[[(3S,5S)-5-[(1R)-1-hydroxy-3-(methylamino)propyl]-3-pyrrolidinyl]thio]-4-methyl-7-oxo-1-azabicyclo[3.2.0]hept-2-ene-2-carboxylic acid), BO 2502A ((4R,5S,6S)-3-[(2S,3'S,4S)-[2,3'-bipyrrolidin]-4-ylthio]-6[(1R)-1-hydroxyethyl]-4-methyl-7-oxo-1-azabicyclo[3.2.0]hept-2-ene-2-carboxylic acid), NE-1530 (3'-sialyllacto-N-neotetraose) PR 39 (L-arginyl-L-arginyl-L-arginyl-L-prolyl-l-arginyl-L-prolyl-L—prolyl-L-tyrosyl-L-leucyl-L-prolyl-L-arginyl-L-prolyl-L-arginyl-L-prolyl-L-prolyl-L-prolyl-L-phenylalanyl-L-phenylalanyl-L-prolyl-L—prolyl-L-arginyl-L-leucyl-L-prolyl-L-prolyl-L-arginyl-L-isoleucyl-L-prolyl-L-prolylglycyl-L-phenylalanyl-L-prolyl-L-prolyl-L-arginyl—L-phenylalanyl-L-prolyl-L-prolyl-L-arginyl-L-phenylalanyl-L-prolinamide [SEQ ID NO: 1]), K130 (5-[[4-[3-[[4-[(4-aminophenyl)sulfonyl]phenyl]amino]propoxy]-3,5-dimethoxyphenyl]methyl]-2,4-pyrimidinediamine), PD 138312 ((R)-7-[3-(1-amino-1-methylethyl)-1-pyrrolidinyl]-1-cyclopropyl-6-fluoro-1,4-dihydro-4-oxo-1,8-naphthyridine-3-carboxylic acid), PD 140248 (7-[(3R)-3-[(1S)-1-aminoethyl]-1-pyrrolidinyl]-1-(2,4-difluorophenyl)-6-fluoro-1,4-dihydro-4-oxo-1,8-naphthyridine-3-carboxylic acid), CP 111905 (5-deoxy-5-[[(2E)-3-[3-hydroxy-4-(2-propenyloxy)phenyl]-2-methyl-1-oxo-2-propenyl]amino]-1,2-O-methylene-D-neo-inositol), Sulopenem ((5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid), ritipenam acoxyl ((5R,6R)-3-[[(aminocarbonyl)oxy]methyl]-6-[(1R)-1-hydroxyethyl]-7-oxo-4-thia-1-azabicyclo[3.2.0]hept-2-ene-2-carboxylic acid (acetyloxy)methyl ester), RO-65-5788 ((6R,7R)-7-[[(2Z)-(5-amino-1,2,4-thiadiazol-3-yl)(hydroxyimino)acetyl]amino]-3-[(E)-[(3'R)-1'-[[(5-methyl-2-oxo-1,3-dioxol-4-yl)methoxy]carbonyl]-2-oxo-[1,3'-bipyrrolidin]-3-ylidene]methyl]-8-oxo-5-thia-1-azabicyclo[4.2.0]oct-2-ene-2-carboxylic acid monosodium salt), Sch-40832 (N-[[48-[1-[[2,6-dideoxy-3-O-(2,6-dideoxy-D-arabino-hexopyranosyl)-D-arabino-hexopyranosyl]oxy]ethyl]-15-ethylidene-1,3a,4,5,10,11,12,13,14,15,19,20,21,22,28, 29,41,42-octadecahydro-41-hydroxy-12,45-bis(1hydroxyethyl)-1-(hydroxymethyl)-22-(1-hydroxy-1-methylpropyl)-36-methyl-51,54,57-tris(methylene)-3-(methlythio)-10,13,20,27,38,49,52,55,58-nonaoxo-18H,27H-5a,29-(iminoethaniminoethanimino ethaniminoethamino([7,2]quinolinomethanoxy methano)-9,6:19,16:26,23:33,30-tetranitrilo-16H,33aH-imidazo[1',5':1,6]pyrido[3,2-m][1,11,17,24,4,7,20,27] tetrathiatetraazacyclotriacontin-1-yl]carbonyl]-2,3-didehydroalanyl-2,3-didehydro-alanine methyl ester stereoisomer), micacocidin A ((OC-6-26-A)-[(4S)-2-[(2S)-2-[(2R,4R)-2-[(4R)-4,5-dihydro-2-[2-hydroxy-.kappa.O)-6-pentylphenyl]-4-thiazolyl-.kappa.N3]-3-methyl-4-thiazolidinyl]-.kappa.N3]-2-(hydroxy-.kappa.O)-1,1-dimethylethyl]-4,5-dihydro-4-methyl-4-thiazolecarboxylato(2-)-.kappa.N3,.kappa-O4]-Zinc), SR-15402 ((1S,5S,8aS,8bR)-1,2,5,6,7,8,8a,8b-octahydro-1-[(1R)-1-hydroxyethytl]-2-oxo-5-[(3S)-3-pyrrolidinylthio]-azeto[2,1-a]isoindole-4-carboxylic acid), TOC 39(1-(2-amino-2-oxoethyl)-4-[[(1E)-2-[(6R,7R)-7-[[(2Z)-(2-amino-4-thiazolyl) (hydroxyimino)acetyl]amino]-2-carboxy-8-oxo-5-thia-1-azabicyclo[4.2.0]oct-2-en-3-yl]ethenyl]thio]-pyridinium inner salt), carumonam ([[(Z)-[2-[[(2S,3S)-2-[[(aminocarbonyl)oxy]methyl]-4-oxo-1-sulfo-3-azetidinyl]amino]-1-(2-amino-4-thiazolyl)-2-oxoethylidene]amino]oxy]-acetic acid), Cefozopran (1-[[(6R,7R)-7-[[(2Z)-(5-amino-1,2,4-thiadiazol-3-yl)(methoxy imino)acetyl]amino]-2-carboxy-8-oxo-5-thia-1-azabicyclo[4.2.0]oct-2-en-3-yl]methyl]-imidazo[1,2-b]pyridazinium inner salt), Cefetamet pivoxil ((6R,7R)-7-[[(2Z)-(2-amino-4-thiazolyl)(methoxy imino)acetyl]amino]-3-methyl-8-oxo-5-thia-1-azabicyclo[4.2.0]oct-2-ene-2-carboxylic acid (2,2-dimethyl-1-oxopropoxy)methyl ester), and T 3811 (des-F(6)-quinolone).

21. The method according to claim 20, wherein said antimicrobial agent is selected from the group consisting of imipenen, amikacin, netilmicin, fosfomycin, gentamicin, teicoplanin, Ziracin, Ly333328, CL331022, HMR3647, Linezolid and Synercid, Aztreonam, and Metronidazole.

22. The method according to claim 14, wherein said subject is selected from a human and an animal.

23. The method according to claim 22, wherein said subject is a human.

24. A compound of the formula

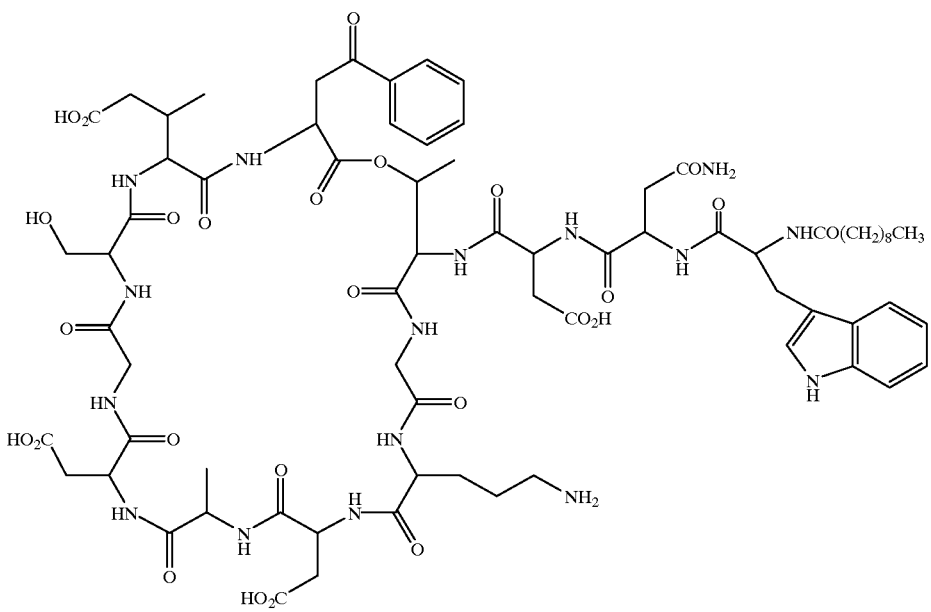
or a salt thereof.
25. A compound of the formula
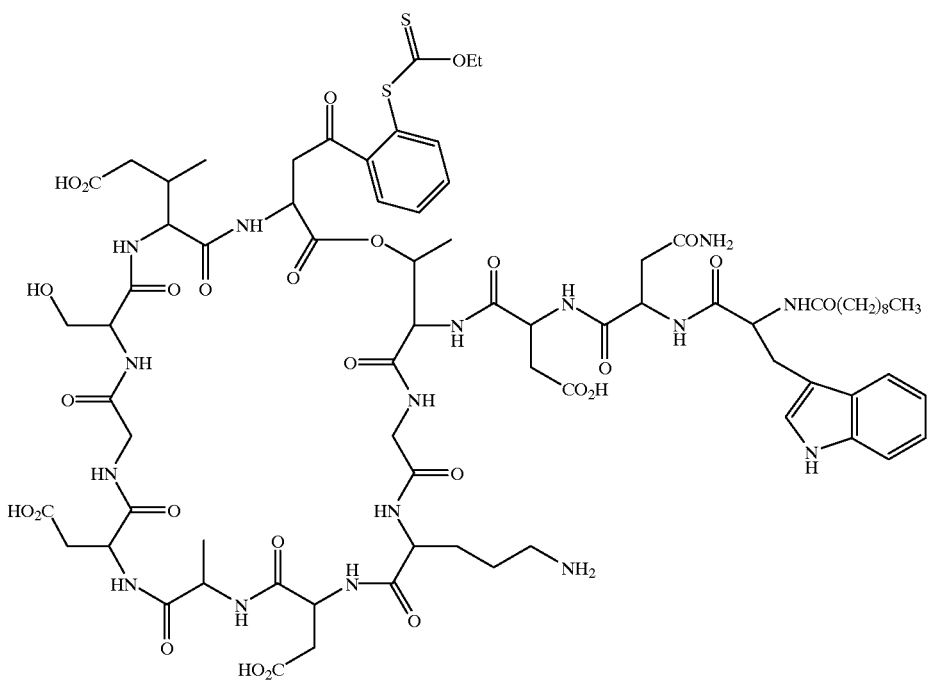
thereof.
26. The method according to claim 20, wherein anti-folate agents are sulfonamides or synthetic antibacterials are selected from nitrofurans, methenamine mandelate and methenamine hippurate.
* * * * *